(12) United States Patent
Smith et al.

(10) Patent No.: US 11,364,005 B2
(45) Date of Patent: Jun. 21, 2022

(54) SYSTEM AND METHOD FOR NAVIGATING X-RAY GUIDED BREAST BIOPSY

(71) Applicant: Hologic, Inc., Marlborough, MA (US)

(72) Inventors: Andrew P. Smith, Lexington, MA (US); Julian Marshall, Los Altos, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 15/031,396

(22) PCT Filed: Oct. 23, 2014

(86) PCT No.: PCT/US2014/061994
§ 371 (c)(1),
(2) Date: Apr. 22, 2016

(87) PCT Pub. No.: WO2015/061582
PCT Pub. Date: Apr. 30, 2015

(65) Prior Publication Data
US 2016/0235380 A1 Aug. 18, 2016

Related U.S. Application Data

(60) Provisional application No. 61/894,947, filed on Oct. 24, 2013.

(51) Int. Cl.
*A61B 6/00* (2006.01)
*A61B 10/02* (2006.01)
(Continued)

(52) U.S. Cl.
CPC ............ *A61B 6/502* (2013.01); *A61B 6/025* (2013.01); *A61B 6/0414* (2013.01); *A61B 6/463* (2013.01);
(Continued)

(58) Field of Classification Search
CPC ....... A61B 6/502; A61B 6/463; A61B 6/5235; A61B 6/481; A61B 6/0414; A61B 6/025; A61B 6/482; A61B 10/0233
See application file for complete search history.

(56) References Cited

U.S. PATENT DOCUMENTS 4,821,727 A 4/1989 Levene et al.
4,907,156 A 6/1990 Doi et al.
(Continued)

FOREIGN PATENT DOCUMENTS

CN 202161328 3/2012
CN 102429678 5/2012
(Continued)

OTHER PUBLICATIONS

Giger, M. et al., "Development of a "smart" workstation for use in mammography", Proceedings of SPIE, (1991), 45: 101-103.
(Continued)

*Primary Examiner* — Jason M Ip
(74) *Attorney, Agent, or Firm* — Merchant & Gould P.C.

(57) ABSTRACT

A method of performing a procedure on a breast of a patient includes compressing the breast of the patient with a paddle of an imaging system and performing an initial imaging procedure on the breast of the patient. The initial imaging procedure includes imaging the breast with an x-ray source at a first energy to obtain a first image and a second energy to obtain a second image. A composite image is generated from the first image and the second image and displayed. A region of interest on the composite image is targeted and a biopsy is performed.

21 Claims, 19 Drawing Sheets

(51) Int. Cl.
*A61B 6/02* (2006.01)
*A61B 6/04* (2006.01)
*A61B 10/00* (2006.01)

(52) U.S. Cl.
CPC .............. *A61B 6/481* (2013.01); *A61B 6/482* (2013.01); *A61B 6/5235* (2013.01); *A61B 6/465* (2013.01); *A61B 10/0041* (2013.01)

(56) References Cited

U.S. PATENT DOCUMENTS

| | | |
|---|---|---|
| 5,078,142 A | 1/1992 | Siczek et al. |
| 5,129,911 A | 7/1992 | Siczek et al. |
| 5,133,020 A | 7/1992 | Giger et al. |
| 5,219,351 A | 6/1993 | Teubner |
| 5,240,011 A | 8/1993 | Assa |
| 5,280,427 A | 1/1994 | Magnusson |
| 5,289,520 A | 2/1994 | Pellegrino et al. |
| 5,343,390 A | 8/1994 | Doi et al. |
| 5,386,447 A | 1/1995 | Siczek |
| 5,415,169 A | 5/1995 | Siczek et al. |
| 5,426,685 A | 6/1995 | Pellegrino et al. |
| 5,491,627 A | 2/1996 | Zhang et al. |
| 5,594,769 A | 1/1997 | Pellegrino et al. |
| 5,609,152 A | 3/1997 | Pellegrino et al. |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,872,828 A | 2/1999 | Niklason et al. |
| 6,022,325 A | 2/2000 | Siczek et al. |
| 6,101,236 A | 8/2000 | Wang et al. |
| 6,102,866 A | 8/2000 | Nields et al. |
| 6,245,028 B1 | 6/2001 | Furst et al. |
| 6,293,282 B1 | 9/2001 | Lemelson |
| 6,459,925 B1 | 10/2002 | Nields et al. |
| 6,468,226 B1 | 10/2002 | McIntyre, IV |
| 6,480,565 B1 | 11/2002 | Ning |
| 6,620,111 B2 | 9/2003 | Stephens et al. |
| 6,626,849 B2 | 9/2003 | Huitema et al. |
| 6,638,235 B2 | 10/2003 | Miller et al. |
| 6,683,934 B1 | 1/2004 | Zhao |
| 6,758,824 B1 | 7/2004 | Miller et al. |
| 6,987,331 B2 | 1/2006 | Koeppe |
| 7,123,684 B2 | 10/2006 | Jing et al. |
| 7,245,694 B2 | 7/2007 | Jing et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,634,050 B2 | 12/2009 | Muller et al. |
| 7,697,660 B2 | 4/2010 | Ning |
| 7,702,142 B2 | 4/2010 | Ren et al. |
| 7,760,924 B2 | 7/2010 | Ruth et al. |
| 7,787,936 B2 | 8/2010 | Kressy |
| 7,831,296 B2 | 11/2010 | DeFreitas et al. |
| 7,869,563 B2 | 1/2011 | DeFreitas |
| 7,991,106 B2 | 8/2011 | Ren et al. |
| 8,532,745 B2 | 9/2013 | DeFreitas et al. |
| 8,594,274 B2 | 11/2013 | Hoernig et al. |
| 9,020,579 B2 | 4/2015 | Smith |
| 9,901,309 B2 | 2/2018 | DeFreitas et al. |
| 10,092,358 B2 | 10/2018 | DeFreitas |
| 10,335,094 B2 | 7/2019 | DeFreitas |
| 10,357,211 B2 | 7/2019 | Smith |
| 10,456,213 B2 | 10/2019 | DeFreitas |
| 10,595,954 B2 | 3/2020 | DeFreitas |
| 2001/0038681 A1 | 11/2001 | Stanton et al. |
| 2002/0113681 A1 | 8/2002 | Byram |
| 2002/0122533 A1 | 9/2002 | Marie et al. |
| 2003/0018272 A1 | 1/2003 | Treado et al. |
| 2003/0073895 A1 | 4/2003 | Nields et al. |
| 2003/0135115 A1 | 7/2003 | Burdette et al. |
| 2004/0077938 A1 | 4/2004 | Mark et al. |
| 2004/0081273 A1 | 4/2004 | Ning |
| 2004/0127789 A1 | 7/2004 | Ogawa |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0084060 A1 | 4/2005 | Seppi et al. |
| 2005/0089205 A1 | 4/2005 | Kapur |
| 2005/0111718 A1* | 5/2005 | MacMahon ............ A61B 6/463 382/130 |
| 2005/0113681 A1 | 5/2005 | Defreitas et al. |
| 2005/0113715 A1 | 5/2005 | Schwindt et al. |
| 2005/0124845 A1 | 6/2005 | Thomadsen et al. |
| 2006/0009693 A1 | 1/2006 | Hanover et al. |
| 2006/0025680 A1 | 2/2006 | Jeune-lomme |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 6/2006 | Miller et al. |
| 2006/0257009 A1 | 11/2006 | Wang |
| 2006/0269040 A1 | 11/2006 | Mertelmeier |
| 2007/0019846 A1 | 1/2007 | Bullitt et al. |
| 2007/0114424 A1 | 5/2007 | Danielsson et al. |
| 2007/0225600 A1 | 9/2007 | Weibrecht et al. |
| 2007/0263765 A1 | 11/2007 | Wu |
| 2008/0019581 A1* | 1/2008 | Gkanatsios ............ A61B 6/025 382/131 |
| 2008/0045833 A1 | 2/2008 | DeFreitas et al. |
| 2008/0101537 A1 | 5/2008 | Sendai |
| 2008/0152086 A1 | 6/2008 | Hall |
| 2008/0187095 A1 | 8/2008 | Boone et al. |
| 2008/0198966 A1 | 8/2008 | Hjarn |
| 2009/0003519 A1* | 1/2009 | Defreitas ................ A61B 6/107 378/37 |
| 2009/0080604 A1 | 3/2009 | Shores et al. |
| 2009/0143674 A1 | 6/2009 | Nields |
| 2009/0171244 A1 | 7/2009 | Ning |
| 2009/0296882 A1 | 12/2009 | Gkanatsios et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1* | 6/2010 | Navab .................... A61B 90/36 600/411 |
| 2010/0208037 A1 | 8/2010 | Sendai |
| 2011/0019891 A1* | 1/2011 | Puong .................... A61B 6/405 382/131 |
| 2011/0069808 A1 | 3/2011 | Defreitas et al. |
| 2011/0087132 A1* | 4/2011 | DeFreitas .............. A61B 90/17 600/567 |
| 2011/0110576 A1* | 5/2011 | Kreeger ................ G16H 50/50 382/132 |
| 2011/0182402 A1 | 7/2011 | Partain |
| 2011/0237927 A1 | 9/2011 | Brooks et al. |
| 2012/0014504 A1* | 1/2012 | Jang ...................... A61B 6/482 378/37 |
| 2012/0134464 A1 | 5/2012 | Hoernig et al. |
| 2012/0238870 A1 | 9/2012 | Smith et al. |
| 2013/0022165 A1* | 1/2013 | Jang ...................... G01N 23/04 378/19 |
| 2013/0044861 A1 | 2/2013 | Muller |
| 2013/0108138 A1* | 5/2013 | Nakayama ............ A61B 6/022 382/132 |
| 2013/0259193 A1 | 10/2013 | Packard |
| 2014/0064444 A1* | 3/2014 | Oh ........................ A61B 6/463 378/37 |
| 2014/0073913 A1 | 3/2014 | DeFreitas et al. |
| 2016/0000399 A1 | 1/2016 | Halmann et al. |
| 2016/0022364 A1 | 1/2016 | DeFreitas et al. |
| 2018/0256118 A1 | 9/2018 | DeFreitas |
| 2019/0015173 A1 | 1/2019 | DeFreitas |
| 2019/0290221 A1 | 9/2019 | Smith |
| 2020/0046303 A1 | 2/2020 | DeFreitas |
| 2020/0093562 A1 | 3/2020 | DeFreitas |
| 2020/0205928 A1 | 7/2020 | DeFreitas |
| 2020/0390404 A1 | 12/2020 | DeFreitas |
| 2021/0000553 A1 | 1/2021 | St. Pierre |
| 2021/0100626 A1 | 4/2021 | St. Pierre |

(56) References Cited

U.S. PATENT DOCUMENTS

FOREIGN PATENT DOCUMENTS

| | | |
|---|---|---|
| DE | 102011087127 | 5/2013 |
| EP | 1428473 | 6/2004 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2003-531516 | 10/2003 |
| JP | 2006-519634 | 8/2006 |
| JP | 2007-130487 | 5/2007 |
| JP | 2009-522005 | 6/2009 |
| JP | 2009-526618 | 7/2009 |
| JP | 2010-137004 | 6/2010 |
| JP | 2012/501750 | 1/2012 |
| JP | 2014-507250 | 3/2014 |
| JP | 2015-506794 | 3/2015 |
| WO | 93/17620 | 9/1993 |
| WO | 94/06352 | 3/1994 |
| WO | 1997/00649 | 1/1997 |
| WO | 00/51484 | 9/2000 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008/054436 | 5/2008 |
| WO | 2009/026587 | 2/2009 |
| WO | 2010/028208 | 3/2010 |
| WO | 2011/043838 | 4/2011 |
| WO | 2012/001572 | 1/2012 |
| WO | 2012/068373 | 5/2012 |
| WO | 2012/112627 | 8/2012 |
| WO | 2012/122399 | 9/2012 |
| WO | 2013/001439 | 1/2013 |
| WO | 2013/078476 A1 | 5/2013 |
| WO | 2013/123091 A1 | 8/2013 |
| WO | 2015/061582 | 4/2015 |
| WO | 2016/103094 | 6/2016 |
| WO | 2016/184746 | 11/2016 |

OTHER PUBLICATIONS

Giger, M. et al., "An "Intelligent" Workstation for Computer-aided Diagnosis", RadioGraphics, (1993), 13(3): 647-656.
European Extended Search Report in Application 14855181.5, dated May 15, 2017, 7 pages.
Japanese Notice of Final Rejection in Application 2016-526115, dated Jun. 24, 2019, 5 pages.
Canadian Office Action in Application 2829349, dated Oct. 15, 2018, 4 pages.
Lewin et al., "Dual-Energy Contrast-Enhanced Digital Subtraction Mammography: Feasibilty", Radiology, Radiological Society of North America, Inc, US, vol. 229, No. 1, Oct. 1, 2003 (Oct. 1, 2003), pp. 261-268, XP 008045080, ISSN: 0033-8419, DOI: 10.1148/RADIOL.2291021276.
PCT Written Opinion in International Application PCT/US2014/061994, dated Jan. 22, 2015, 4 pages.
PCT International Preliminary Report on Patentability in International Application PCT/US2014/061994, dated Apr. 26, 2016, 5 pages.
Chinese 2nd Office Action in Application 201480058064.5, dated Jul. 16, 2019, 5 pgs.
"Filtered Back Projection", (NYGREN), published May 8, 2007, URL: http://web.archive.org/web/19991010131715/http://www.owlnet.rice.edu/~elec539/Projects97/cult/node2.html, 2 pgs.
Berg WA et al., "Combined screening with ultrasound and mammography vs mammography alone in women at elevated risk of breast cancer", JAMA 299:2151-2163, 2008.

Carton AK, et al., "Dual-energy contrast-enhanced digital breast tomosynthesis—a feasibility study", Br J Radiol. Apr. 2010;83 (988):344-50.
Chen SC, et al., "Initial clinical experience with contrast-enhanced digital breast tomosynthesis", Acad Radio. Feb. 2007 14(2):229-38.
Diekmann F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain C., et al., "Contrast-enhanced digital mammography", Eur J Radiol. 2009; 69:34-42.
EP Extended Search Report dated Jul. 18, 2014 in EP App 12754521.8.
European Communication in Application 10707751.3, dated Oct. 4, 2018, 5 pages. (corresponding to .0020USU1 matter).
European Communication in Application 10707751.3, dated Aug. 7, 2019, 6 pages.
European Extended Search Report for European Patent Application No. 14770362.3 dated Sep. 28, 2016, 8 pgs.
European extended Search Report in Application 18153706.9, dated Jun. 1, 2018, 8 pages.
European Mar. 23, 2009 European Search Report in connection with counterpart Europeanpatent Application No. 07750818.
European Office Action in Application 10707751.3, dated Feb. 19, 2018, 5 pgs.
Freiherr G., "Breast tomosynthesis trials show promise", Diagnostic Imaging—San Francisco 2005, V27; N4:42-48.
Hologic, "Lorad StereoLoc II" Operator's Manual 9-500-0261, Rev. 005, 2004, 78 pgs.
ICRP Publication 60: 1990 Recommendations of the International Commission on Radiological Protection.
Jochelson M., et al., Bilateral, RSNA 2010, 96th Scientific Assembly and Scientific Meeting.
Jong, RA, et al., Contrast-enhanced digital mammography: initial clinical experience. Radiology 2003; 228:842-850.
Kopans, et.al. Will tomosynthesis replace conventional mammography? Plenary Session SFN08: RSNA 2005.
Lehman CD, et al. MRI evaluation of the contralateral breast in women with recently diagnosed breast cancer. N Engl J Med 2007; 356:1295-1303.
Lindfors KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Observations by Third Party, Remarks concerning European patent application No. 10707751.3 according to Article 115 EPC, dated Apr. 24, 2014, 8 pgs.
PCT Feb. 20, 2008 International Search Report and Written Opinion in connection with corresponding International patent application No. PCT/US2007/04006, 7 pgs.
PCT International Search Report and Written Opinion in Application PCT/US2010/025873, dated Aug. 2, 2010, 19 pgs.
PCT International Search Report in Application PCT/US2014/026164, dated Jul. 28, 2014, 1 page.
PCT International Written Report for International Application PCT/US2014/026164, dated Jul. 28, 2014, 12 pgs.
PCT/US12/28334 International Search Report and Written Opinion, dated Jul. 5, 2012.
Poplack SP, et al., Digital breast tomosynthesis: initial experience in 98 women with abnormal digital screening mammography. AJR Am J Roentgenology Sep. 2007 189(3):616-23.
Prionas ND, et al., Contrast-enhanced dedicated breast CT: initial clinical experience. Radiology. Sep. 2010 256(3):714-723.
Rafferty E. et al. Assessing Radiologist Performance Using Combined Full-Field Digital Mammography and Breast Tomosynthesis Versus Full-Field Digital Mammography Alone: Results . . . presented at 2007 Radiological Society of North America meeting, Chicago IL.
Shrading, Simone et al., "Digital Breast Tomosynthesis-guided Vacuum-assisted Breast Biopsy: Initial Experiences and Comparison with Prone Stereotactic Vacuum-assisted Biopsy", the Depart-

(56) References Cited

OTHER PUBLICATIONS ment of Diagnostic and Interventional Radiology, Univ. of Aachen, Germany, published Nov. 12, 2014, 10 pgs.

Smith, A., Full field breast tomosynthesis. Radiol Manage. Sep.-Oct. 2005; 27(5):25-31.

Weidner N, Semple JP, Welch WR, Folkman J. Tumor angiogenesis and metastasis: correlation in invasive breast carcinoma. New England Journal of Medicine 1991; 324:1-8.

Weidner N, The importance of tumor angiogenesis: the evidence continues to grow. Am J Clin Pathol. Nov. 2004 122(5):696-703.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

"Supersonic to feature Aixplorer Ultimate at ECR", AuntiMinnie.com, 3 pages (Feb. 2018).

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Dromain, Clarisse et al., "Dual-energy contrast-enhanced digital mammography: initial clinical results", European Radiology, Sep. 14, 2010, vol. 21, pp. 565-574.

Reynolds, April, "Stereotactic Breast Biopsy: A Review", Radiologic Technology, vol. 80, No. 5, Jun. 1, 2009, pp. 447M-464M, XP055790574.

Burbank, Fred, "Stereotactic Breast Biopsy: Its History, Its Present, and Its Future", published in 1996 at the Southeastern Surgical Congress, 24 pages.

E. Shaw de Paredes et al., "Interventional Breast Procedure", published Sep./Oct. 1998 in Curr Probl Diagn Radiol, pp. 138-184. (D15 in opposition).

European Communication in Application 19213173.8, dated Apr. 20, 2021, 5 pages.

European Extended Search Report in Application 19213173.8, dated Apr. 7, 2020, 7 pages.

European Notification of a Notice of Opposition in Application 14855181.5, dated Sep. 8, 2020, 77 pages.

European Observations by Third Party, Remarks, and Acknowledgment concerning European patent application No. 19213173.8, according to Article 114(2) EPC, dated Aug. 4, 2021, 8 pgs.

European Summons to Attend Oral Proceedings in Application 14855181.5, dated Apr. 19, 2021, 25 pages.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009. (Reference labeled D10 in 01 Opposition).

European Decision Revoking the European Patent EP 3060132 B in EP Application 14855181.5, dated Feb. 23, 2022, 56 pages.

\* cited by examiner

SYSTEM AND METHOD FOR NAVIGATING X-RAY GUIDED BREAST BIOPSY

This application is a National Stage Application of PCT/US2014/061994, filed Oct. 23, 2014, which claims benefit of U.S. Provisional Patent Application No. 61/894,947, filed Oct. 24, 2013 and which applications are incorporated herein by reference. To the extent appropriate, a claim of priority is made to each of the above disclosed applications.

INTRODUCTION

Mammography is a well-established method of breast imaging which may be used for breast cancer screening and diagnosis. Screening mammograms are preferably obtained annually for female members of the population over the age of forty, or those having a genetic risk of breast cancer. Should masses or calcifications ('regions of interest') be identified during a screening mammogram, the patient may require further diagnosis. Such diagnosis may involve biopsying the region of interest and analyzing excised tissue. As used herein, the term "region of interest" can mean a mass or calcification, or a specific area or target within the breast that may contain such a mass or calcification.

Various imaging modalities have historically been used during breast biopsies. The imaging modalities include ultrasound imaging, x-ray imaging and magnetic resonance imaging. Performing a breast biopsy typically involves positioning the patient, visualizing the region of interest using the imaging equipment, targeting coordinates of the region and retrieving cells or tissue from the targeted region. Cells or tissue may be retrieved in a variety of ways, including through open surgery, fine needle aspiration, core needle biopsy or vacuum assisted biopsy. Open surgery, the most invasive procedure, is generally performed by a radiologist placing a wire into the breast during visualization of the region of interest, where the wire extends into the region that is to be excised. The patient is then transferred to surgery and tissue is retrieved using the wire to locate the region of interest.

X-ray imaging in stereotactic mode is generally used for breast biopsies because it is desirable to visualize and target regions in a three dimensional volume. Stereotactic biopsies obtain volume information using x-ray images taken in at least two planes. The x-ray images are then processed to localize a target region of interest in three-dimensional space using the principal of parallax to determine the depth, or Z dimension, of the target region.

Various approaches to breast biopsies with three dimensional imaging have included use of breast tomosynthesis. Nonlimiting examples of such approaches include U.S. Patent Application Publication Nos. 2008/0045833, 2011/0087132, and 2012/0238870, the disclosures of which are hereby incorporated in their entireties. Three-dimensional imaging is described generally in PCT Publication No. WO 2013/123091, the disclosure of which is hereby incorporated in its entirety. Although tomosynthesis-guided biopsy represents a simplified approach to targeting and imaging during biopsy procedures, the first image presented is typically a reconstructed slice within the tissue, either adjacent to the compression paddle or to the breast tray, and, thus, the lesion of interest may not necessarily be in view in the first image presented.

SUMMARY

What is needed, then, is an image guided biopsy approach that targets and presents the lesion reliably, accurately, and consistently, preferably, in the first image presented, similar to that of conventional stereotactic biopsy.

According to an aspect of the technology, targeting and biopsying of a lesion or feature of interest in a breast is facilitated by presenting a synthesized mammogram (e.g., for pre-verification, post-verification, or both) to a user in which the synthesized mammogram can be generated from 2D and/or 3D images (e.g., projection and/or reconstructed tomosynthesis images) of the breast. A biopsy window is optionally included in the user interface to indicate to a user whether the lesion or feature of interest has been correctly targeted. The lesion or feature of interest can be highlighted or featured in the synthesized mammogram. In such instances, a user can optionally select the lesion or feature of interest in the user interface and then the user can be taken to a relevant slice in the tomo stack (e.g., one the presents the lesion or feature of interest best or one that is right above or below the slice in the tomo stack that best presents the lesion or feature of interest. Optionally, an indication can be provided to the user if a lesion or feature of interest is not presented in the synthesized mammogram.

Additionally or alternatively, according to the aspect of the technology, targeting and biopsying of a lesion or feature of interest in a breast is facilitated with a contrast agent in conjunction with or alternatively to dual energy imaging in which the imaging is 2D, 3D, or both. The contrast image, dual energy image, or high energy image is then presented to the user to target and commence biopsy of the lesion or feature of interest. In an embodiment, where the acquired images are 3D images (used with a contrast agent and/or dual energy), a synthesized mammogram can be presented to the user.

In another aspect, the technology relates to a method of performing a procedure on a breast of a patient, the method includes: compressing the breast of the patient with a paddle of an imaging system; performing an initial imaging procedure on the breast of the patient, wherein the initial imaging procedure includes imaging the breast with an x-ray source at a first energy to obtain a first image and a second energy to obtain a second image; generating a composite image from the first image and the second image; displaying the composite image; targeting a region of interest on the composite image; and performing a biopsy on a target location. In an embodiment, the method includes using information from the composite image to define the target location. In another embodiment, the method further includes, after performing the biopsy on the target location, imaging the breast with the x-ray source at a third energy to obtain a third image. In yet another embodiment, the method for targeting the region of interest includes: identifying the region of interest visible in the first image; and correlating the region of interest with a reference object visible in the second image. In still another embodiment, the method further includes locating an indicator proximate the region of interest on the composite image.

In another embodiment of the above aspect, the method further includes storing coordinates of the region of interest. In an embodiment, the method further includes positioning a biopsy needle based at least in part on the stored coordinates. In another embodiment, the method includes injecting the patient with a contrast agent prior to imaging at the first energy, such that the contrast agent is visible in the first image. In yet another embodiment, the first energy is greater than the second energy. In still another embodiment, the composite image is at least one of a 2D image, a 3D image, and a synthesized 2D image.

In another embodiment of the above aspect, the composite image includes a plurality of tomosynthesis images. In an embodiment, the method further includes simultaneously displaying the first image and the second image. In another embodiment, the method further includes displaying an overlay of the first image and the second image.

In another aspect, the technology relates to a method of performing a procedure on a breast of a patient, the method includes: compressing the breast of the patient with a paddle of an imaging system; imaging the breast with an x-ray source at a first energy to obtain a first image; imaging the breast with the x-ray source at a second energy to obtain a second image; identifying at least one difference between the first image and the second image, wherein the difference corresponds to a region of interest; and performing a biopsy on the region of interest. In an embodiment, the method includes: generating a composite image from the first image and the second image; displaying the composite image; and displaying the region of interest on the composite image. In another embodiment, the first energy is greater than the second energy. In yet another embodiment, the method further includes injecting the patient with a contrast agent prior to imaging the breast at the first energy. In still another embodiment, the method further includes, after performing the biopsy, imaging the breast with the x-ray source at a third energy to obtain a third image. In yet another embodiment, the method further includes displaying the third image.

In another aspect, the technology relates to a method of performing a procedure on a breast of a patient, the method includes: compressing the breast of the patient with a paddle of an imaging system; delivering a plurality of x-ray energies to the breast from an x-ray source, so as to obtain a plurality of images; identifying at least one difference between the plurality of images, wherein the difference corresponds to a region of interest; displaying at least one image of the breast; identifying the region of interest on the displayed image; and performing a biopsy on the region of interest.

BRIEF DESCRIPTION OF FIGURES

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the technology. In the figures, each identical or nearly identical component that is illustrated in various figures is represented by a like numeral. For purposes of clarity, not every component may be labeled in every figure. In the figures.

DETAILED DESCRIPTION

Figure 1:
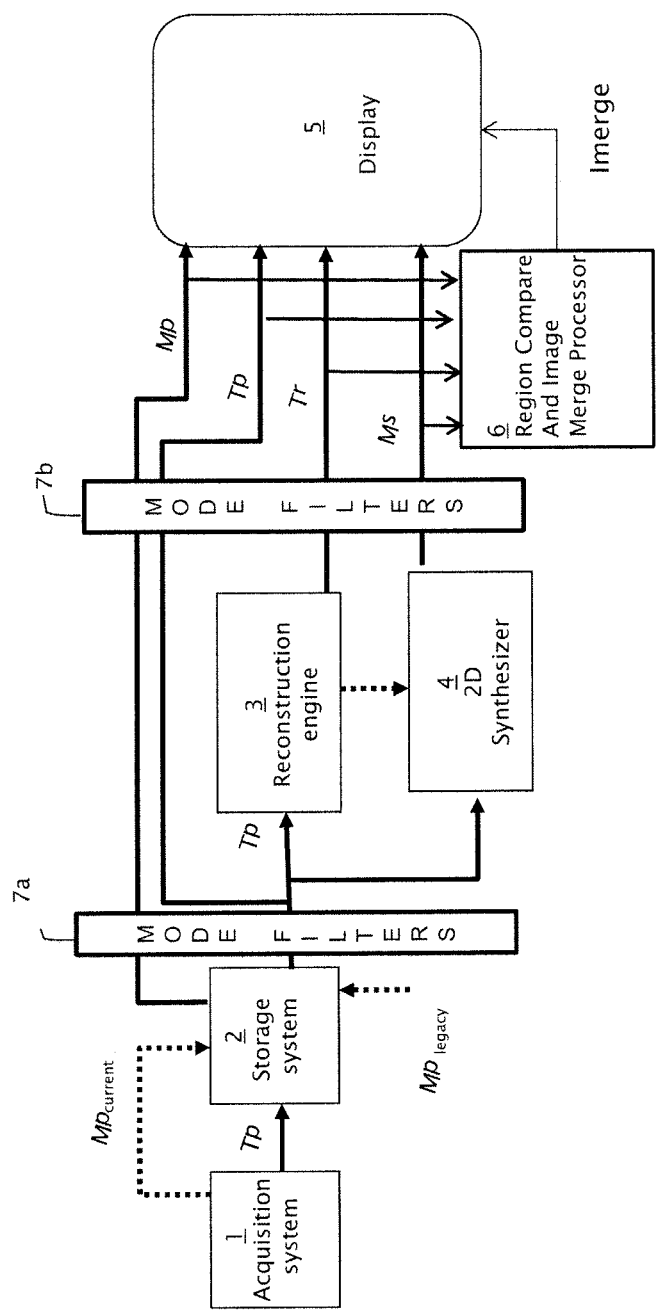
FIG. 1 is a block diagram illustrating the flow of data through a system that includes a combination mammography/tomosynthesis acquisition system and/or a tomosynthesis-only acquisition system to acquire tomosynthesis and/or mammography (including contrast mammography) images of a patient's breast, and further includes one or more processors that implement the image merge technology of the presently disclosed technologies for providing a two dimensional synthesized image by importing the most relevant data from the acquired 2D and/or 3D source images into a single merged 2D image for display to a medical professional.

Except as otherwise noted, the articles "a," "an," and "the" mean "one or more."

While the existing and proposed systems for x-ray mammography and tomosynthesis offer many advantages, it is believed that a need still exists for further improvements to make mammography/tomosynthesis more useful for image guided breast biopsies, and that it is particularly desirable to make it possible to use the same system in different modes of operation and thereby reduce acquisition and operating costs and provide greater clinical value and convenience.

Described herein include examples of systems and methods for multi-mode breast x-ray imaging. A single system carries out breast imaging in modes that include standard mammography, diagnostic mammography, dynamic imaging such as with a contrast agent and at different x-ray energies, tomosynthesis imaging, combined standard and tomosynthesis imaging during a single breast compression, tomosynthesis guided biopsies, biopsies guided by synthesized mammograms, biopsies guided by dynamic imaging, and stereotactic imaging with a biopsy station mounted to the system.

In an example of such a system, a compression arm assembly for compressing and immobilizing the breast for x-ray imaging, an x-ray tube assembly, and an x-ray image receptor can be angled relative to each other for different imaging protocols and modes. They can be independently rotated and synchronized as needed, or can be mechanically linked for appropriate synchronized rotation. A patient shield can be optionally mounted to the compression arm assembly to provide a mechanical interlock against patient contact with the rotating x-ray tube assembly. An anti-scatter grid can be used that can cover the imaging area of the x-ray receptor in some or all of the modes but can be configured to be retracted completely outside the imaging area for other modes.

In describing the depicted embodiments of the disclosed technologies illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

The following abbreviations shall have the following definitions throughout this patent specification. Mp refers to a conventional mammogram or contrast enhanced mammogram, which are two-dimensional (2D) projection images of a breast, and encompasses both a digital image as acquired by a flat panel detector or another imaging device, and the image after conventional processing to prepare it for display and/or storage or other use. Tp refers to an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display and/or storage or other use. Tr refers to an image that is reconstructed from tomosynthesis projection images Tp, for example, in the manner described in one or more of U.S. Patent Application Publication No. 2010/0135558, U.S. Pat. Nos. 7,760,924, 7,616,801, and 7,577,282, and PCT International Patent Publication Nos. 2013/078476 and 2013/123091, the disclosures of which are fully incorporated by reference herein in their entirety, wherein a Tr image represents a slice of the breast as it would appear in a projection x ray image of that slice at any desired angle, not only at an angle used for acquiring Tp or Mp images. Ms refers to synthesized 2D images, which simulate mammography images, such as a craniocaudal (CC) or mediolateral oblique (MLO) images, and are constructed using tomosynthesis projection images Tp, tomosynthesis reconstructed images Tr, or a combination thereof. Examples of methods that may be used to generate Ms images are described in the above-incorporated U.S. Patent Application Publication No. 2010/0135558, U.S. Pat. No. 7,760,924, and PCT International Patent Publication Nos. 2013/078476 and 2013/123091. IMERGE refers to a 2D image constructed by importing into a single image one or more objects and/or regions from any two or more of Mp, Ms, Tp or Tr images of a patient's breast, wherein an image from which an object or region is imported into the merged image comprises a source image for that object or region, and wherein objects or regions are imported into the merged image at X,Y coordinate locations corresponding to the X,Y coordinate locations of the objects or regions in their respective source image.

The terms IMERGE, Tp, Tr, Ms and Mp each encompasses information, in whatever form, that is sufficient to describe the respective image for display, further processing, or storage. The respective IMERGE, Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to x rays of corresponding volumes in the breast, i.e., voxels or columns of tissue. In a preferred embodiment, the geometry of the tomosynthesis images (Tr and Tp), mammography images (Ms and Mp) and the merged image IMERGE are matched to a common coordinate system, as described in U.S. Pat. No. 7,702,142, the disclosure of which is hereby incorporated by reference in its entirety. Unless otherwise specified, such coordinate system matching is assumed to be implemented with respect to the embodiments described in the ensuing detailed description of this patent specification.

FIG. 1 illustrates the flow of data in an exemplary image generation and display system, which incorporates the merged image generation and display technology and features of the presently disclosed technologies. It should be understood that, while FIG. 1 illustrates a particular embodiment of a flow diagram with certain processes taking place in a particular serial order or in parallel, various other embodiments of the presently disclosed technologies are not limited to the performance of the image processing steps in any particular order, unless so specified.

More particularly, the image generation and display system includes an image acquisition system 1 that acquires tomosynthesis image data for generating Tp images of a patient's breasts, using the respective three dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend Mplegacy in FIG. 1) in a storage device 2, which is preferably a DICOM-compliant Picture Archiving and Communication System (PACS) storage device. Following acquisition, the tomosynthesis projection images Tp may also be transmitted to the storage device 2 (as shown in FIG. 1).

The Tp images are transmitted from either the acquisition system 1, or from the storage device 2, or both, to a computer system configured as a reconstruction engine 3 that reconstructs the Tp images into reconstructed image "slabs" Tr, representing breast slices of selected thickness and at selected orientations, as disclosed in the above-incorporated patents and application publication. The imaging and display system 1 further includes a 2D synthesizer that operates substantially in parallel with the reconstruction engine for generating 2D images that simulate mammograms taken at any orientation (e.g., CC or MLO) using a combination of one or more Tp and/or Tr images. The synthesized 2D images may be generated dynamically prior to display (as shown in FIG. 1) or may be stored in storage system 2 for later use. The synthesized 2D images are interchangeably referenced as T2d and Ms. The reconstruction engine 3 and 2D synthesizer are preferably connected to a display system 5 via a fast transmission link. The originally acquired Mp and/or Tp images may also be forwarded to the display system 5 for concurrent or toggled viewing with the respective Tr and/or Ms images by a medical professional.

Mode filters 7a, 7b are disposed between image acquisition and image display. Each of the filters 7a and 7b may additionally include customized filters for each type of image (i.e., Tp, Mp, Tr) arranged to identify and highlight certain aspects of the respective image types. In this manner, each imaging mode can be tuned or configured in an optimal way for a specific purpose. The tuning or configuration may be automatic, based on the type of the image, or may be defined by manual input, for example through a user interface coupled to a display. In the illustrated embodiment of FIG. 1, the filters 7a and 7b are selected to highlight particular characteristics of the images that are best displayed in the respective imaging mode, for example, geared towards highlighting masses or calcifications, or for making the merged image (described below) appear to be a particular image type, such as a 3D reconstructed slice, or a 2D mammogram.

According to one aspect of the disclosed technologies, and as described in greater detail herein, the system 1 includes an image merge processor 6 that merges relevant image data obtained from a set of available source and synthesized images of a patient's breast to provide a merged 2D image IMERGE for display. The set of available images used to generate the merged image IMERGE may include filtered and/or unfiltered Ms, Mp, Tr and/or Tp images. While FIG. 1 depicts all these types of images being input into the image merge processor 6, it is also envisioned within the scope of the disclosed technologies that the merged mage may be manually configurable. For example, a user interface or preset configuration may be provided and configured to allow a user to select a particular group of two or more images or image types for generating a synthesized 2D image IMERGE for display.

By way of illustration, a medical professional, such as a radiologist, may wish to merge two or more reconstructed tomosynthesis slices (or slabs) in order to provide a merged image showing the most readily discerned structures in the collective tomosynthesis image data in a displayed synthesized 2D image, which essentially maps the tomosynthesis slices (or slabs) at a pixel wise granularity. Additionally or alternatively, the radiologist may combine a 2D mammogram image, whether Mp or Ms, with a 3D projection, or with selected reconstructed images, in order to obtain a customized merged image that highlights both calcifications and various tissue structures in the breast. Filters applied to each type of image can further highlight the types of structures or features in the merged image that are generally most prevalent or most readily discerned in the respective source image type. Thus, one type of filter may be applied to mammography images to highlight calcifications, while a different filter may be applied to tomosynthesis slices to highlight masses, allowing both the highlighted calcifications and highlighted tissue masses to be displayed in the single merged image. Filters may also provide the merged image with a desired look and feel; i.e., to make the merged image appear more like a tomosynthesis or mammography image.

The display system 5 may be part of a standard acquisition workstation (e.g., of acquisition system 1), or of a standard (multi-display) review station that is physically remote from the acquisition system 1. In some embodiments, a display connected via a communication network may be used, for example, a display of a personal computer or of a so-called tablet, smart phone or other hand-held device. In any event, the display 5 of the system is preferably able to display IMERGE, Ms, Mp and Tr (and/or Tp) images concurrently, e.g., in separate side-by-side monitors of a review workstation, although the technology may still be implemented with a single display monitor, by toggling between images.

To facilitate the detection/diagnosis process, Tr slices are preferably reconstructed all to the same size for display, which can be the same as the size of an Mp or Ms image of the breast, or they can be initially reconstructed to sizes determined by the fan shape of the x ray beam used in the acquisition, and then later converted to that same size by appropriate interpolation and/or extrapolation. In this manner, images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image being concurrently displayed, or with which the displayed image is, or can be, toggled.

For example, if two images of the same breast are taken and are not the same size, or do not have the same resolution, provisions may be made to automatically or user-selectively increase or reduce the magnification (i.e., "zoom in" or "zoom out") of one or both images, such that they appear to be the same size when they are concurrently displayed, or as a user toggles between the images. Known interpolation, extrapolation and/or weighting techniques can be used to accomplish the re-sizing process, and known image processing technology can also be used to make other characteristics of the displayed images similar in a way that facilitates detection/diagnosis. When viewing such resized images, according to one embodiment of the disclosed technologies, the merged image IMERGE is automatically resized, accordingly.

Thus, the system 1, which is described as for purposes of illustration and not limitation in this patent specification, is capable of receiving and displaying selectively tomosynthesis projection images Tp, tomosynthesis reconstruction images Tr, a synthesized mammogram image Ms, and/or mammogram (including contrast mammogram) images Mp, or any one or sub combination of these image types. The system 1 employs software to convert (i.e., reconstruct) tomosynthesis images Tp into images Tr, software for synthesizing mammogram images Ms, and software for merging a set of images to provide a merged image that displays, for every region of the merged image, the most relevant feature in that region among all images in the source image set. For the purpose of this patent specification, an object of interest or feature in a source image may be considered a 'most relevant' feature for inclusion in the merged image based upon the application of one or more CAD algorithms to the collective source images, wherein the CAD algorithms assign numerical values, weights or thresholds, to pixels or regions of the respective source images based upon identified/detected objects and features of interest within the respective region or between features or, in instances when the merged image is generated directly from the synthesized image without CAD assistance, simply the pixel value, weight or other threshold associated with a pixel or region of the image. The objects and features of interest may include, for example, spiculated lesions, calcifications, and the like. Various systems and methods are currently well known for computerized detection of abnormalities in radiographic images, such as those disclosed by Giger et al. in RadioGraphics, May 1993, pp. 647-656; Giger et al. in Proceedings of SPIE, Vol. 1445 (1991), pp. 101-103; U.S. Pat. Nos. 4,907,156, 5,133,020, 5,343,390, and 5,491,627, each of which being hereby incorporated by reference in its entirety.

Figure 2:
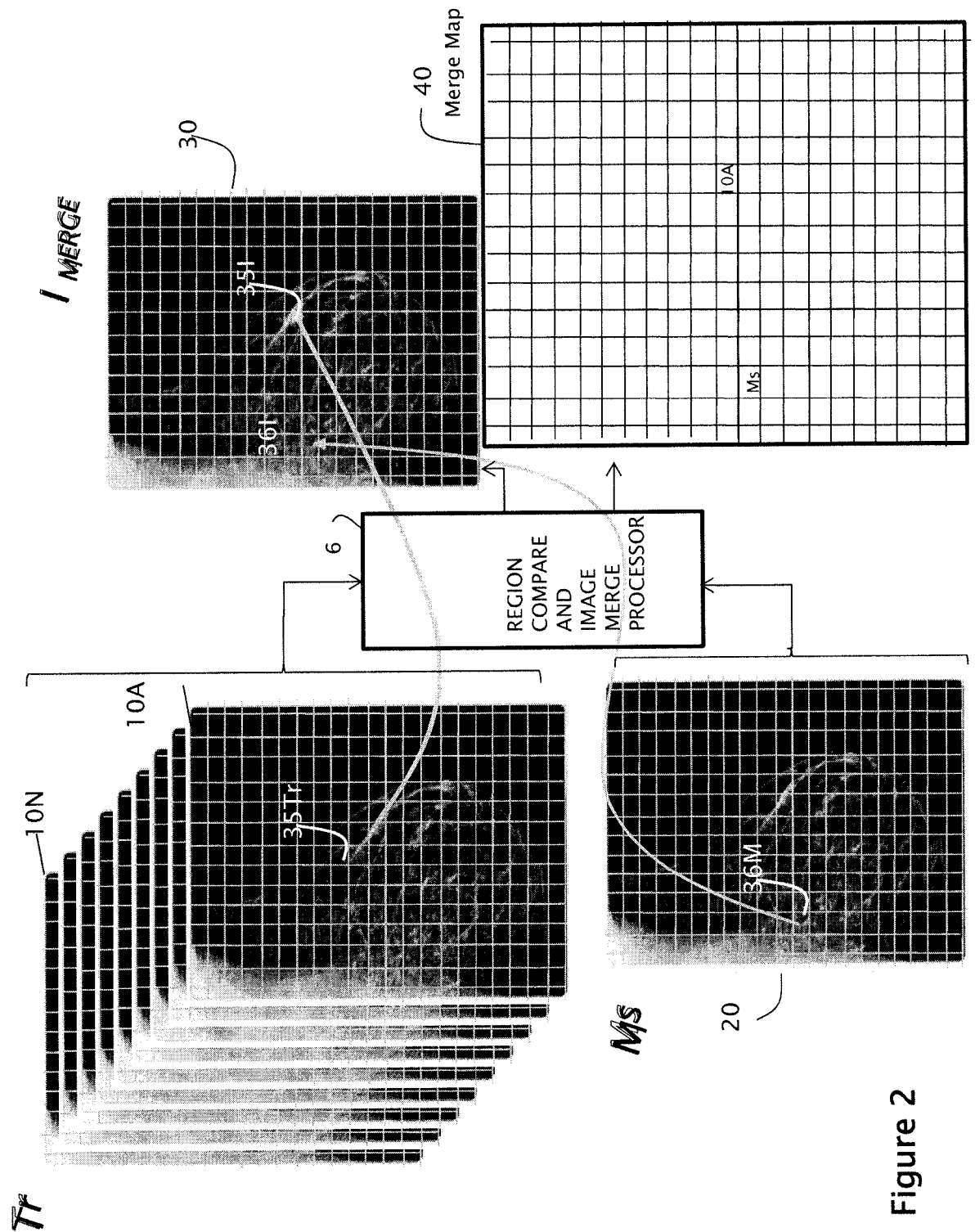
FIG. 2 is a diagram illustrating the data flow of a series of tomosynthesis slices and a synthesized 2D mammogram through the image merge technology of the presently disclosed technologies to generate a merged image and a corresponding merge (or "guidance") map.

FIG. 2 is a diagram which pictorially illustrates the merging of image data from a tomosynthesis reconstruction image data set Tr, comprising tomosynthesis slices 10A to 10N, with image data from a mammogram 20, in this case a synthesized mammogram Ms. For ease of description, filters are not shown in this example. The tomosynthesis image data set Tr and synthesized mammogram Ms are forwarded to the region compare and image merge processor 6, which evaluates each of the source images for which a merged image is to be generated (i.e., whether automatically, or based on a specific user commend) in order to (1) identify the objects and features of interest in each image for those that may be considered a "most relevant" feature for possible inclusion in the merged image based upon the application of one or more CAD algorithms (as described above), (2) identifies respective pixel regions in the images that contain the identified features, and (3) thereafter compares the images on a region by region basis, searching for that image with the most desirable display data for each respective region.

Figure 3:
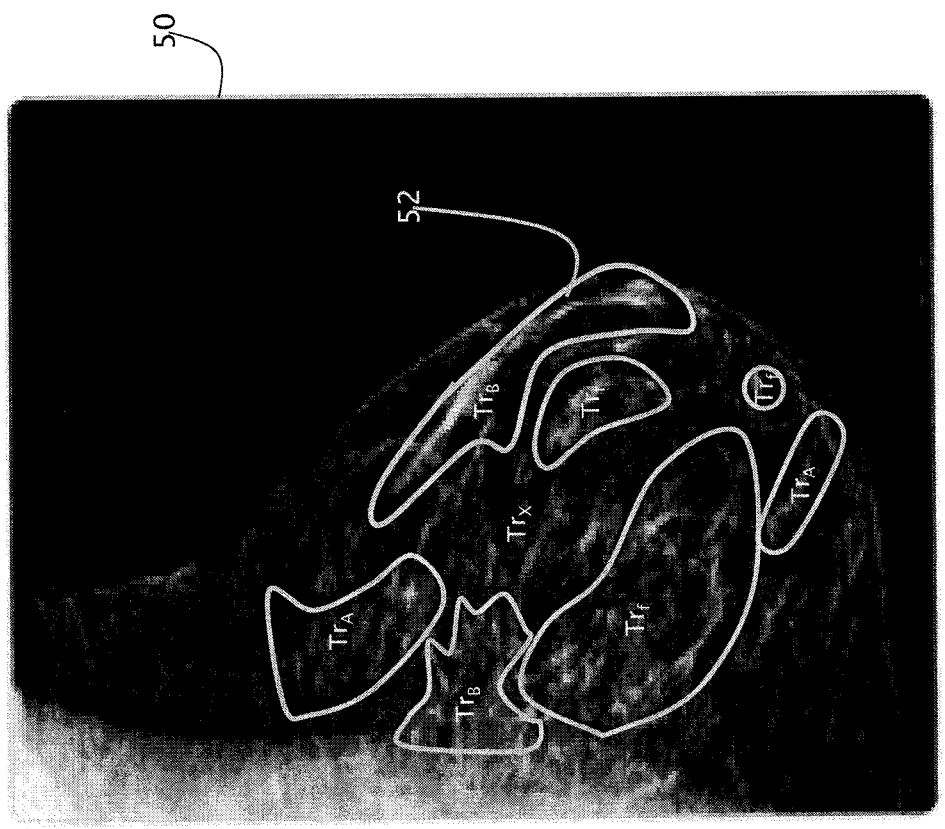
FIG. 3 depicts one embodiment of a displayed merged image, wherein certain region boundaries are dynamically identified during merge image build.

As discussed above, the image with the most desirable display data may be an image with a highest pixel value, a lowest pixel value, or which has been assigned a threshold value or weight based on the application of a CAD algorithm to the image. When the image with the most desirable display data for that region is identified, the pixels of that region are copied over, or added in with higher weight, to the corresponding region of the merged image. For example, as shown in FIG. 2, region 36M from image Ms is written to region 36I. Region 35 of tomosynthesis slice 10A is copied to region 35I of the merged image. Although the regions of FIG. 2 are shown as pre-defined grid regions, it is not necessary that regions be pre-defined in this manner. Rather, according to one aspect of the disclosed technologies, the boundaries of the regions may be dynamically identified during the region compare and image generation process by performing comparisons at pixel or multi-pixel granularities. By way of illustration, FIG. 3 illustrates a merged image 50, which has been constructed via the combinations of numerous regions of different source images, at arbitrary region boundaries, for example, which may be identified according to the detection of particular features within the respective source images.

Figure 4:
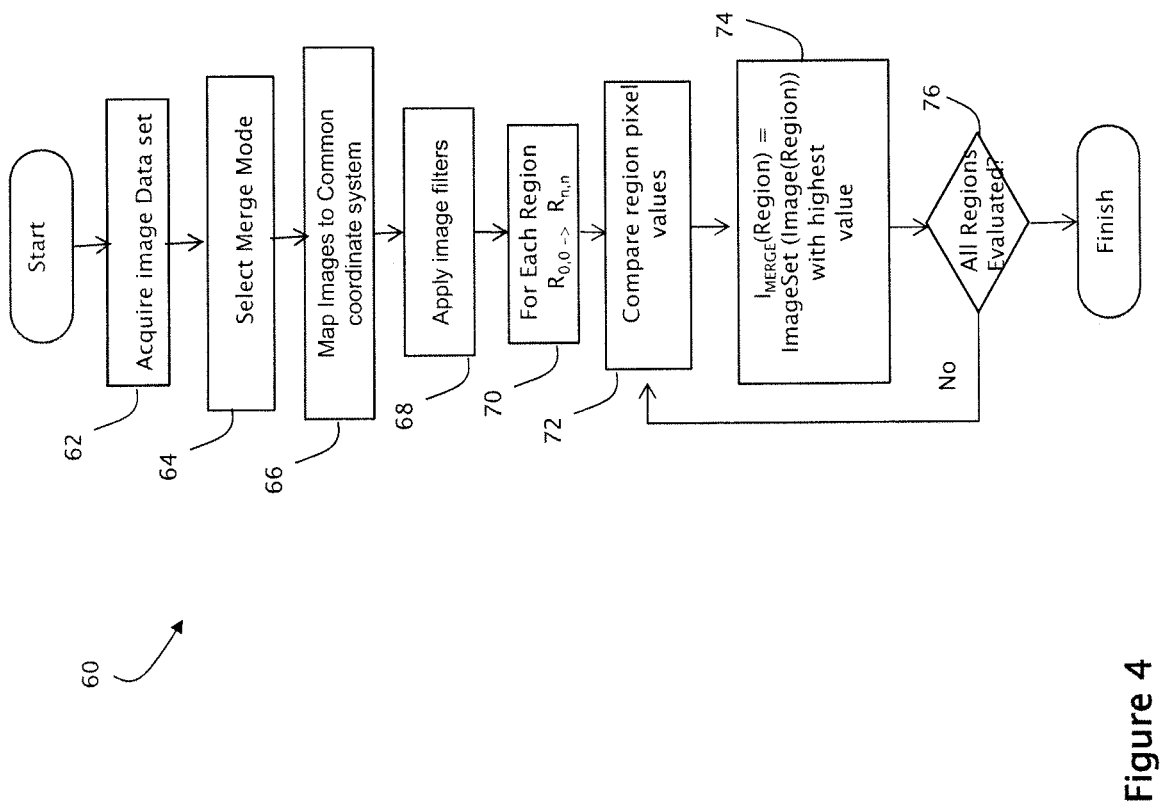
FIG. 4 is a flow diagram illustrating exemplary steps performed during an image merge process according to one embodiment of the presently disclosed technologies.

FIG. 4 is a flow diagram provided to illustrate exemplary steps that may be performed in an image merge process carried out in accordance with one embodiment of the disclosed technologies. At step 62, an image data set is acquired. The image data set may be acquired by a tomosynthesis acquisition system, a combination tomosynthesis/mammography system, or by retrieving pre-existing image data from a storage device, whether locally or remotely located relative to an image display device. At step 64, a user may optionally select a merge mode, wherein the user may designate (1) which images are to be used for the source image set to generate the merged image, (2) whether to highlight certain features in the merged image, such as calcifications, spiculated lesions or masses, and (3) whether to display the image as a lower resolution tomosynthesis image, etc. At step 66, the images that are to be merged to generate the merged image are mapped to a common coordinate system, for example, as described in the above-incorporated U.S. Pat. No. 7,702,142. Other methods of matching images of different coordinate systems may alternatively be used. At step 72, the process of comparing regions among the different images begins. At step 74, each IMERGE region is populated with the pixels of the region of an image from the source image set having the most desirable pixels, value, or pattern. The process of populating regions continues until it is determined, at step 76, that all regions have been evaluated, at which point the merged image is ready for display.

Figure 5A:
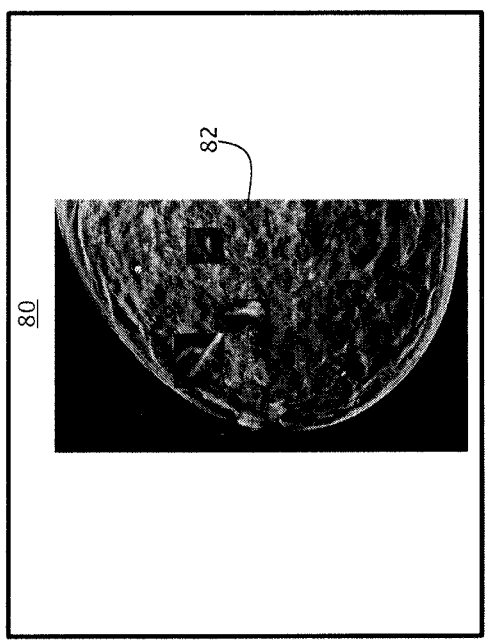
FIGS. 5A and 5B illustrate one embodiment of a display of a merged image, and a resultant display of a source image in response to selection of a region in the merged image by a user.
Figure 5B:
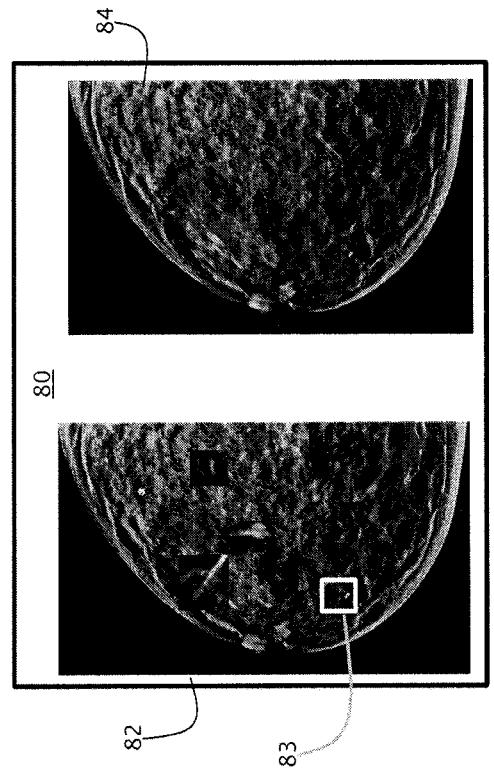

Once the merged image is generated, it may be used to assist in the navigation through a tomosynthesis image data stack from which the merge image was generated. Such navigation is a two-step process comprising selection of various objects of interest, and display of corresponding tomosynthesis images that are the source of such objects of interest in the merged image. By way of example, FIG. 5A and FIG. 5B illustrate two views of a display 80. The first view of display 80 shown in FIG. 5A illustrates a merged image 82, having regions sourced by different ones of an acquired or synthesized image set. FIG. 5B illustrates a particular feature enabled by the presently disclosed technologies, whereby a user may select a region or area 83 within the merged image 82, and the resulting image source 84 for that area is presented to the user.

The presently disclosed technologies envision many different mechanisms for selection of the objects of interest and corresponding display of the respective source images corresponding; although it is to be understood that the disclosed technologies are not limited to those described herein. For example, the selection of a region or area within the merged image may include a selection of a CAD mark, or alternatively a selection of a particular feature of interest to the reviewer. Although in both instances the most relevant slices are made available to the user, the mechanics behind the processes differ. One such preferred mechanism is illustrated in FIG. 2. As the regions of the merged image are populated, a merge (or "guidance") map 40 is also constructed. The merge map stores, for each region of the merged image, an identifier of the image from which the region is sourced. Therefore, as shown in FIG. 2, the Ms identifier is stored in region 36, while the 10A TR slice identifier is stored in region 35. As will be described in more detail herein, the merged map may be used during the display of the merged image to permit fast viewing of the respective source image(s) for user-selected regions or objects of interest.

Selection Using CAD Marks:

In addition or alternatively to use of a merge/guidance map, if the merged image is presented with a CAD overlay, the CAD overlay may include either CAD marks derived from 3D data, or CAD marks derived from 2D data (if the system has the ability to obtain 2D data). CAD marks derived from 3D data generally include, as part of the data object associated with the mark, identifiers of one or more slices which contributed to the generation of the 3D mark. When the merged image is overlaid with 3D CAD data, selection of the CAD mark results in the retrieval of the series of slices that contributed to the mark. In one embodiment, the central image slice is displayed; in alternate embodiments, the image slice having the highest weight is displayed; and in a still further alternate embodiment, the image slice having the least visual noise (i.e., the clearest image) is displayed.

Selection by Objects of Interest:

As an alternate to selecting by CAD marks, a mechanism is provided for allowing a user to select any object on a merged image, whether it is a CAD mark, or a feature of interest, such as any abnormality or irregularity in the image. In one embodiment, the user or system may select a region, using for example a mouse click for a single pixel area, or a click and drag action to select a larger region. Alternatively, the user may be provided with a selection of graphical frames of various or variable sizes, and have the ability to move the frame to different locations within the merged image to select areas when it is desired to view additional tomosynthesis image slices. In response to such a selection, the particular image slice for initial display may be selected in a variety of ways.

For example, an image slice could be selected based on the weighting of its associated pixel within the selected region. Or a particular image slice may be selected because a particular feature which is selected, or which is near a pixel or region that is selected, is best viewed in the selected image slice, e.g., provides the clearest view of that region. Thus, the identification of a particular image slice that is most relevant to a selected pixel or region may utilize pixel information that surrounds the selected object, for example, using region growing techniques known to those in the art. Thus, pixels that neighbor the selected pixel or region are included in the evaluation for relevant slices if the pixels have a characteristic that satisfies a certain threshold established by the user; for example, including but not limited to the pixels having a particular weight, or being arranged in a particular pattern, etc.

Alternatively, a group of image slices may be selected, e.g., a successive order of image slices, with a central slice or most heavily weighted slice being first presented. As described above, alternatively the image slice within the group having the least noise, i.e., the clearest slice, may be provided. In addition, the selection of an image slice for presentation may also take into account a desired visualization mode. Thus, if the user-specified purpose is to visualize calcifications, an image slice having calcification features may be presented ahead of another slice within the group having a lesser calcification characteristic.

It will be appreciated that the disclosed and described systems and methods in this patent specification are designed to condense the image information made available from a tomosynthesis reconstruction volume (or "stack") containing a patient's 3D breast image data down to a single, synthesized 2D image, similar to a conventional 2D mammographic image. By reviewing this synthesized 2D image concurrently with the 3D tomosynthesis stack, it is possible to provide a much more efficient and accurate review of the patient's breast tissue. This is because the synthesized 2D merged image can act as a guidance-map, so that the medical professional reviewing the images can focus on the synthesized 2D image for detecting any objects or regions of interest that merit further review, and the system can provide immediate, automated navigation to a "best" corresponding tomosynthesis image slice (or a subset of adjacent tomosynthesis slices) to allow the medical professional to conduct this further review, verify and evaluate the finding. Thus, it is preferred, although not required for practicing all embodiments of the disclosed technologies, for the medical professional to employ a user interface that can display a respective synthesized 2D merged image along-side the tomosynthesis volume image slices, for concurrent viewing of both.

Figure 6:
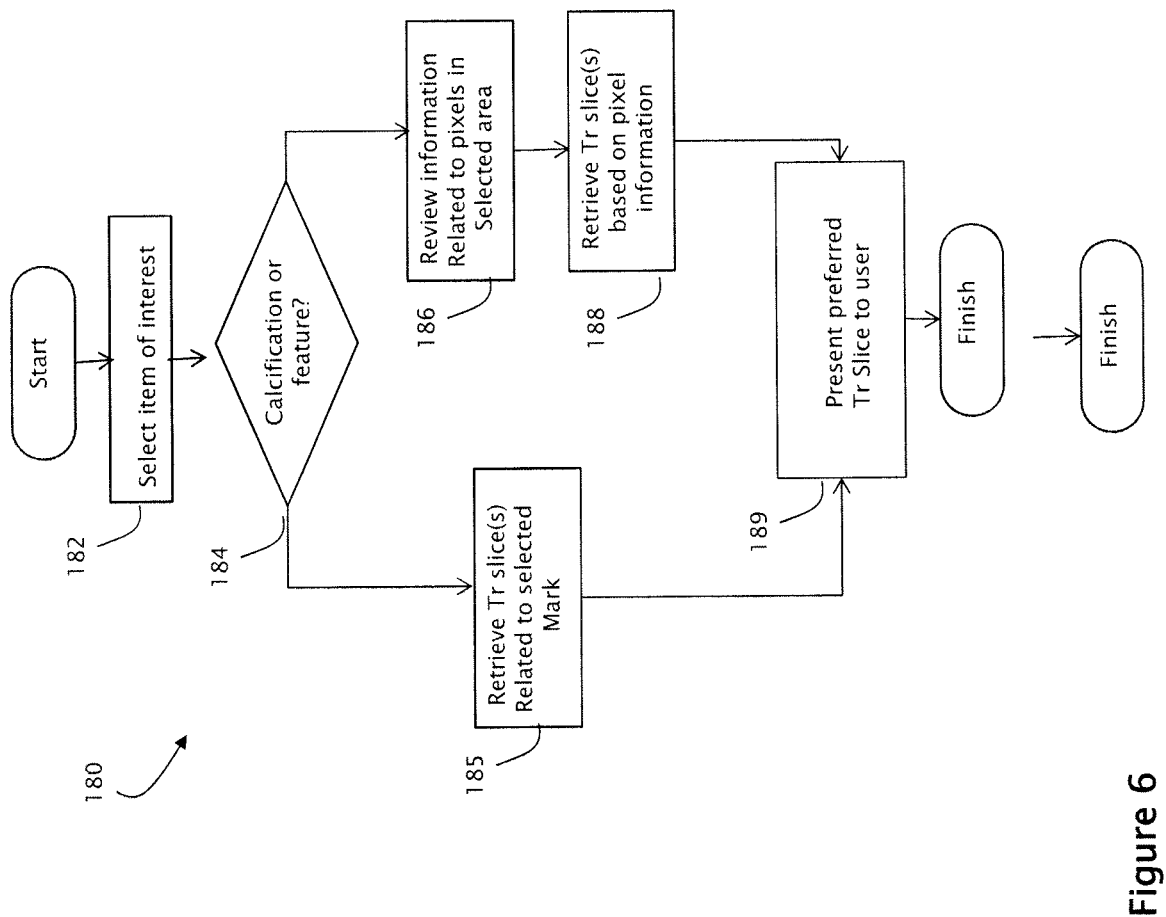
FIG. 6 is flow diagram illustrating an exemplary process for retrieving and presenting a reconstructed tomosynthesis image slice in response to user-selection of an object of interest in a synthesized 2D image, according to one embodiment of the presently disclosed technologies.

FIG. 6 illustrates one exemplary process 180 for retrieving and presenting a Tr image slice in response to user-selection of an object of interest in a merged image, which may be implemented using a software program according to one embodiment of the presently disclosed technologies. The process 180 operates, in response to a selection of an object of interest in a merged image at step 182. At step 184, the process determines whether the selected object is a CAD mark or a non-CAD mark feature of interest. If it is a CAD mark, at step 185, the Tr slices related to the CAD mark are retrieved. At step 189, one of the Tr slices is selected and presented for display based on at least one of its relative position in the stack, relative weight of the voxel value of the slice, a selected visualization mode, etc. If, at step 184, the process determines that the selected object was a non-CAD mark feature of interest, then at step 186, the source Tr images associated with the selected region are evaluated, and a particular Tr source is selected for display based on its relative voxel value as compared to voxel values in other Tr sources that map to the region. It is noted that the Tr sources that contribute to pixel values within a selected region may be intermittently spaced within the 3D tomosynthesis volume. Thus, when the most relevant Tr source image is selected, it may be presented either alone, or as part of a stack of images together with one or more neighboring Tr slice images. The most relevant Tr source may be the presented image, or alternatively another image in the stack associated with the most relevant image may be first presented, for example if that particular image is clearer.

Figure 7:
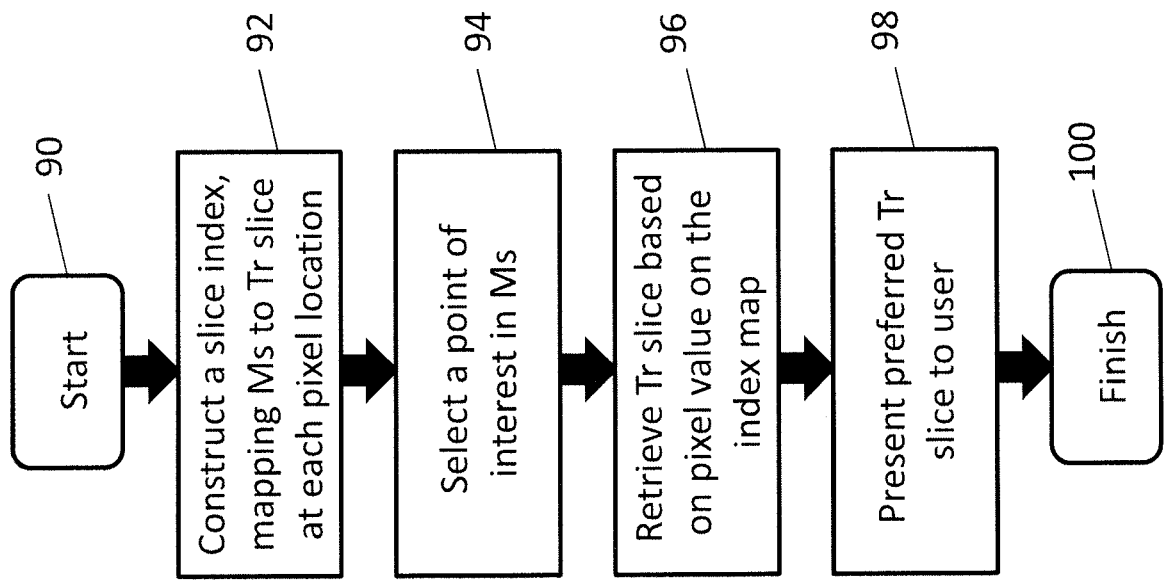
FIG. 7 is a flow diagram illustrating another exemplary process for retrieving and presenting a reconstructed tomosynthesis image slice in response to user-selection of an object of interest in a synthesized 2D image, according to another embodiment of the presently disclosed technologies.

FIG. 7 depicts another process that may be software-implemented for using a synthesized 2D image for navigating a 3D tomosynthesis image stack ("tomosynthesis stack" or "tomo stack"), according to another embodiment of the presently disclosed technologies. At initiation or activation 90, the process includes, at step 92, constructing a tomosynthesis image slice index map, wherein the pixel locations of the synthesized 2D image are mapped to corresponding pixel locations in pertinent image slices of the tomosynthesis stack. In particular, the tomosynthesis stack index map includes identifying information of selected tomosynthesis slice images from the breast volume stack that are source images or that otherwise contain a most similar representation of regions and/or objects displayed in the synthesized 2D image. The tomosynthesis stack index map is preferably generated prior to when a medical professional is ready to conduct his or her review of the breast image data. The details for constructing the tomosynthesis stack index map, in accordance with one preferred embodiment, are described below in conjunction with FIG. 8.

Figure 9:
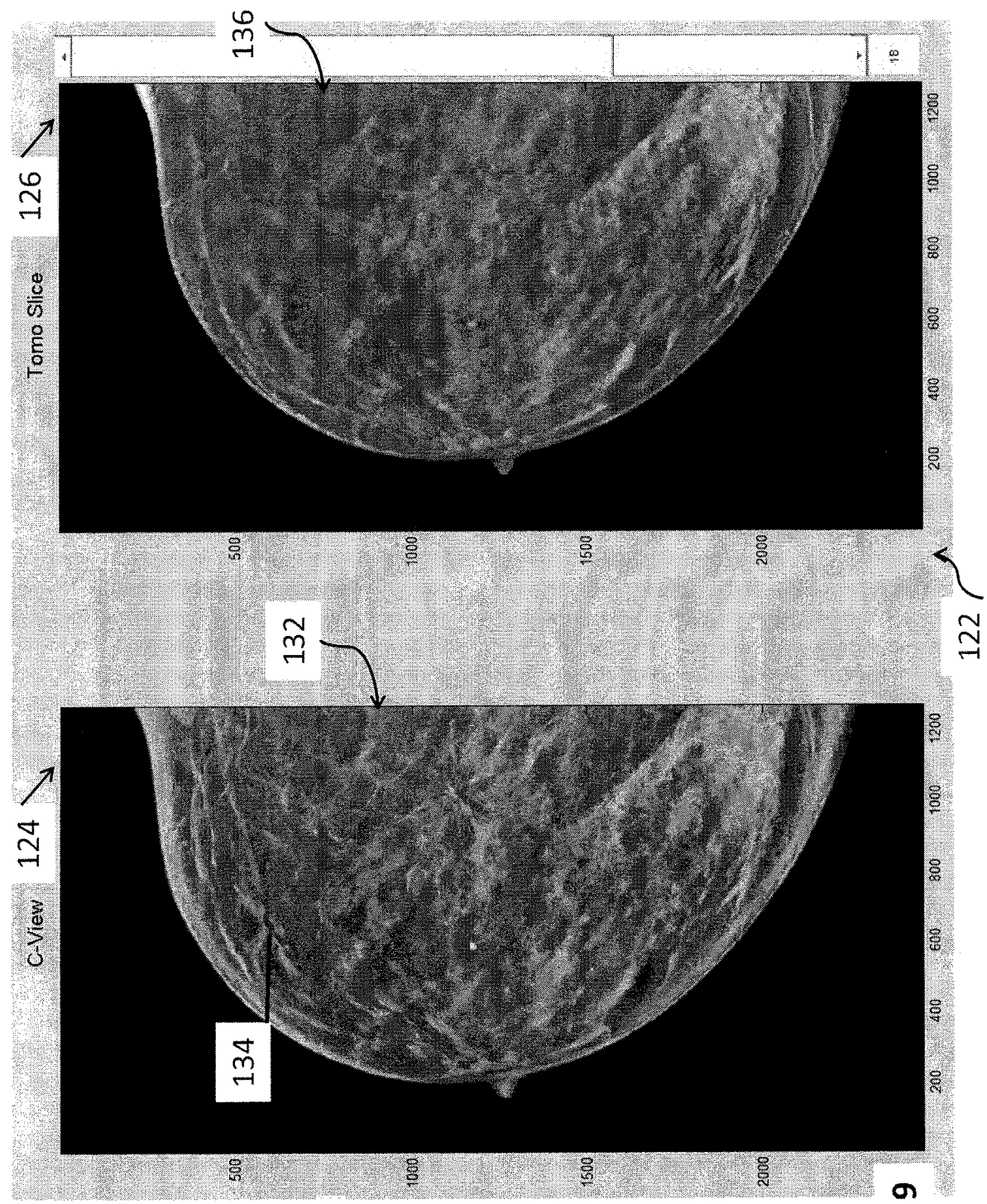
FIG. 9 depicts an exemplary user interface, including a left-hand side monitor displaying a synthesized 2D image of a patient's breast, including a highlighted tissue structure, wherein the highlighting is in the form of a contour line that represents a boundary of the highlighted tissue structure, and a right-hand side monitor displaying the tomosynthesis image from which the highlighted tissue structure was imported into the 2D image, or which otherwise provides a best view of the highlighted tissue structure.
Figure 10:
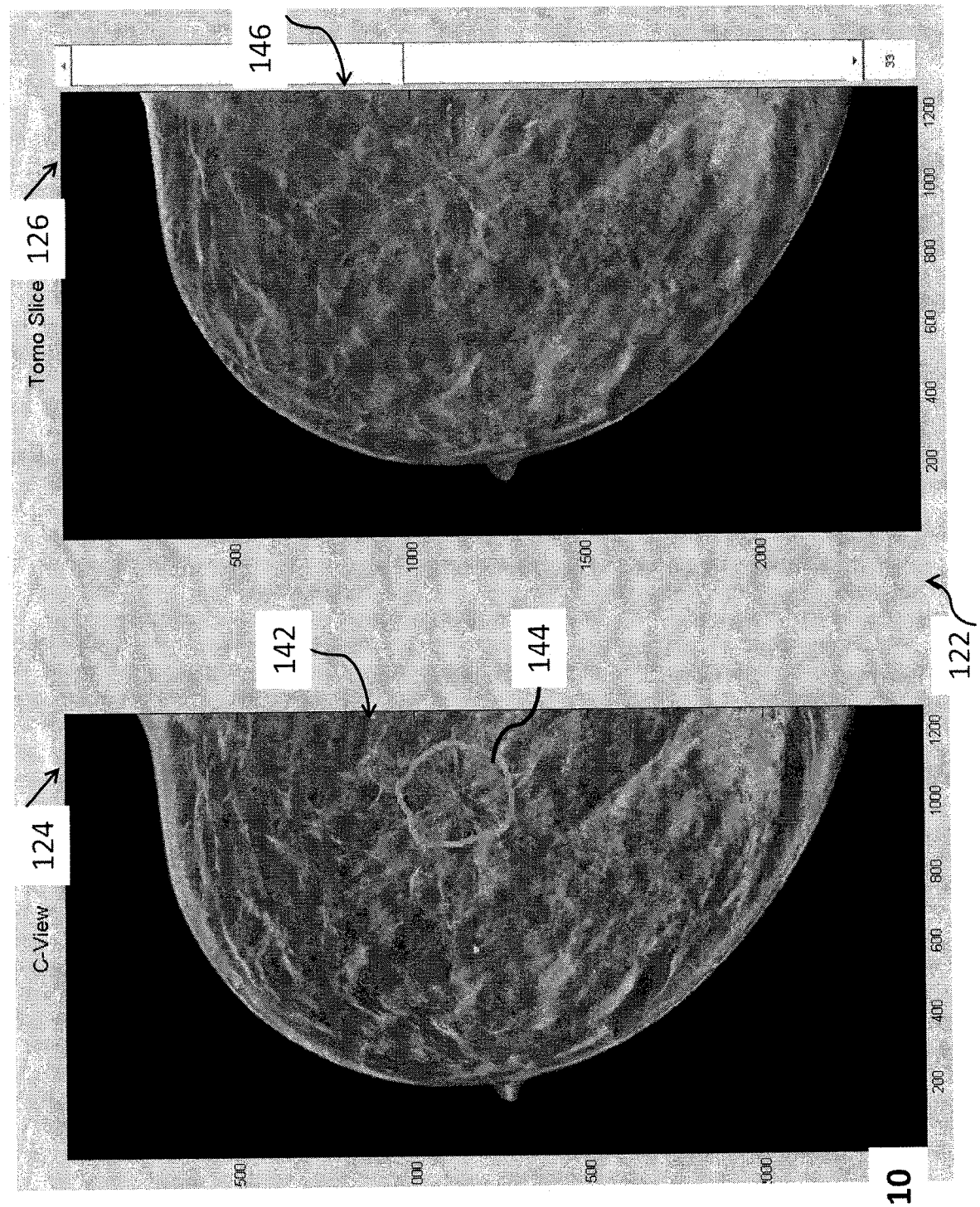
FIG. 10 depicts the user interface of FIG. 9, again displaying a synthesized 2D image of a patient's breast including a highlighted spiculated mass in the left-hand monitor, and a right-hand side monitor displaying the tomosynthesis image from which the depicted spiculated mass was imported into the 2D image, or which otherwise provides a best view of the spiculated mass.
Figure 11:
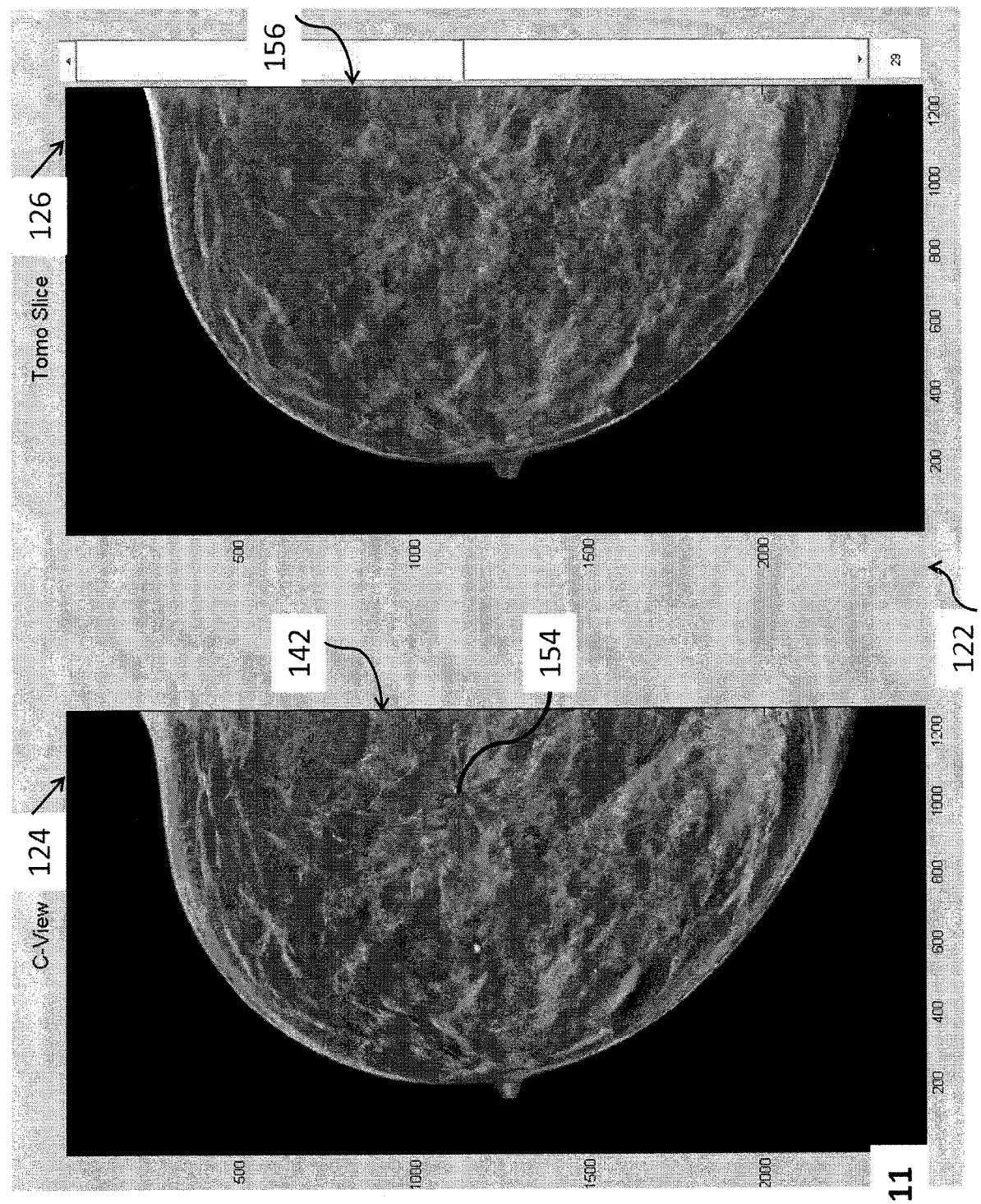
FIG. 11 depicts the user interface of FIG. 10, including the same breast image displayed in the left-hand side monitor, but now highlighting a region containing micro-calcifications, with the right-hand side monitor displaying the tomosynthesis image from which the highlighted region containing the micro-calcifications was imported into the 2D image, or which otherwise provides a best view of the micro-calcifications.

The synthesized 2D image is displayed to the medical professional (interchangeably referred to as the "user" of the described system), typically on a workstation having side-by-side monitors as depicted in FIGS. 9-11. Depending on how the user has configured the workstation, when initiating review of particular patient breast image data, only the synthesized 2D image may be presented, e.g., on the left-hand-side monitor, with the right-hand-side monitor being blank, or perhaps depicting a first or middle image slice from the tomosynthesis stack, preferably depending on a user-selectable configuration. In one embodiment, the system will initially display the synthesized 2D image on the left-hand-side monitor, and a "most relevant" one of the tomosynthesis slice images on the right-hand-side monitor, which was determined by the system based upon the displayed tomosynthesis slice being most similar in appearance to the synthesized 2D image, or having the relatively most interesting objects, out of the tomosynthesis image stack for the entire breast volume.

Thereafter, the medical professional (user) may use the user-interface to activate the navigational capability of the system. In particular, at step 94, the user may affirmatively input a command to select a particular object or region in the displayed synthesized 2D image. Alternatively, the system may be configured so that the user merely positions a "pointer," e.g., a movable cross or arrowhead that is controlled using a mouse or similar input device), overlying an object or region in the displayed synthesized 2D image, thereby "indicating" an interest in the item. In response to the received command or indication, using the index map, the system may easily retrieve, at step 96, and display on the right-hand-side monitor, at step 98, the tomosynthesis slice that is either the direct source of the user selected/indicated object or region, or which otherwise contains a most similar representation of the object or region as depicted in the displayed 2D image. Additionally and/or alternatively, the system may be configured for concurrently displaying a respective source image and/or most similar representation of a tissue structure or region that corresponds to a given location of a user movable input device in the displayed synthesized 2D image.

The plurality of 2D and/or 3D images from which a synthesized 2D image is generated may include tomosynthesis projection images, tomosynthesis reconstruction slices, mammography images, contrast enhanced mammography images, synthesized 2D images, and combinations thereof. It will be appreciated that the synthesized 2D image advantageously incorporates the most relevant information from each of the underlying acquired and computer generated image data sets of the patient's breast. Thus, different regions of pixels in the displayed synthesized 2D image may be sourced from corresponding different images in the underlying image data set, depending on which underlying image is best for viewing an object of interest, e.g., a mass or a calcification, in the respective region. The particular regions may be identified statically, i.e., within a particular grid, or dynamically, i.e., based on identified objects of interest, and may range in granularity from as little as one pixel, to all pixels in the respective image. In one embodiment, priority is given to first importing into a merged image under construction those regions containing one or more specific tissue structures of interest in the images of a tomosynthesis image data set (or "stack"), and thereafter populating the remaining regions of the merged image with the otherwise most relevant regions from the images, as described above.

The user interface may additionally include features to enable the medical professional to manipulate the presented tomosynthesis data, for example, to allow the medical professional to scan through adjacent image slices of the tomosynthesis stack, or to further zoom (magnify) into a selected region, to place markers, or alternatively to apply filters or other image processing techniques to the image data. In this manner, the medical professional may quickly review a large stack of tomosynthesis data by utilizing a synthesized 2D image for navigation purposes, thereby increasing the performance and efficiency of breast cancer screening and diagnosis. According to a further aspect of the disclosed technologies, it has been determined or otherwise appreciated that particular types of images may include or be superior for viewing different types of relevant information. For example, calcifications are typically best visualized in 2D mammograms, while masses are typically best visualized using 3D reconstructed images.

Thus, in one embodiment of the disclosed technologies, different filters are applied to each of the different types of underlying 2D and/or 3D images in the image data set used to generate the merged image, the filters selected to highlight particular characteristics of the images that are best displayed in the respective imaging mode. Appropriate filtering of the images prior to generating the merged image helps ensure that the final merged image includes the most relevant information that can be obtained from all the underlying image types. Additionally and/or alternatively, the type of filtering performed for the various images may be defined via user input, which permits a user to select a 'merge mode', for example, geared towards highlighting masses, calcifications, or for making the merged image appear to be a particular image type, such as a 3D reconstructed slice, or a 2D mammogram.

Synthesizing the 2D image may be accomplished in a variety of ways. For example, in one embodiment, general purpose image filtering algorithms are used to identify features within each of the respective 2D and 3D images, and a user may select whether to use 2D filtered data or 3D filtered data to generate the merged image. Alternatively, 2D or 3D filtered data may be automatically selected in accordance with a particular visualization mode that has been user selected; for example, 2D filtered data may be automatically selected by the system for calcification visualization mode, while 3D filtered data may be automatically selected by the system for mass visualization modes. In one embodiment, two different merged images may be constructed, one for each mode; alternatively, a single merged image may be constructed that takes into account the respective filtered image data results, from all available image types.

In one embodiment, features (representing potential objects of interest) are identified in the available source images and thereafter weighted, e.g., on a pixel by pixel or region by region basis in each respective image. A 2D image is then constructed by incorporating the respective regions having the most significant weight in individual images of the available source images. The size of the region may vary in granularity from one pixel to many (or even all) pixels of the respective image, and may be statically pre-defined, or may have margins that vary in accordance with the varying thresholds of the source images. The synthesized (aka "merged") image may be pre-processed and stored as a DICOM object following tomosynthesis acquisition, and thereafter forwarded with the reconstruction data for subsequent review by a medical professional. Such an arrangement removes the need to forward weighting information for each reconstructed slice. Alternatively, the stored DICOM object may include the weighting information, allowing the merged image to be dynamically constructed in response to a request for a synthesized 2D image at the medical professional's work station. In one embodiment, both the weighting information and the synthesized 2D image may be provided in the DICOM object, allowing presentation of a default merged image, while still enabling customization according to the personal workflow of the reviewer. To be clear, the weighting information can be stored with the image itself, and need not be a separate file.

It is realized that the visualization of the synthesized 2D images may have some drawbacks. For example, there may be neighboring regions in the merged image which exhibit bright calcifications, but which in fact are sourced from image slices that are distant from one another in the z plane. Therefore, what may appear to be a cluster of micro-calcifications in the 2D image may, in fact, be individual calcifications that are distributed (i.e., along the z-axis) throughout the breast and thus do not actually represent a micro-calcification cluster that requires further review. Thus, according to a further aspect of the disclosed technologies, a 'cluster spread indicator' may be provided with the synthesized 2D image, which visually indicates the distribution of calcifications along the z-plane, allowing the medical professional to quickly assess whether a group of calcifications comprise a calcification cluster.

In some instances, the system may determine based on the index map information that more than one tomosynthesis image slice should be displayed for a selected/indicated object type or region, for example, a spiculated mass. In such instances, a series of two or more adjacent tomosynthesis slices are displayed, one after the other, at a timing interval that is preferably user selected. As will be additionally described herein, the user may select or indicate more than one object or region in a given synthesized 2D image. Once the user has completed his or her review of the displayed tomosynthesis slice(s), the process is complete (at step 100) for the particular breast image data.

As previously pointed out, while various image processing techniques may be employed for providing this navigational functionality, in a preferred embodiment, the system is preferably configured for, and the method further includes, generating an index map comprising identifying information of selected images of the plurality of 2D and/or 3D images that are source images or that otherwise contain a most similar representation of regions and/or objects displayed in the synthesized 2D image. The index map can thereafter be used by the system to greatly reduce the time needed to navigate through the images, e.g., a tomosynthesis volume stack of the breast image volume.

An implementation of one preferred process 102 for generating an index map will now be described in conjunction with the flow diagram shown in FIG. 8. Two parallel processes are initially employed. In one process, the image data contained in the synthesized 2D image 104 is mapped to selected tomosynthesis image slices of a 3D volume 106 to construct a "generic" index map 108. In particular, the pixel locations in the 2D image 104 is mapped to the pixel locations in the respective 3D (tomosynthesis) images 106 based entirely on image similarity, akin to the pieces of a jigsaw puzzle. In other words, the generic index map 108 is based entirely on best-fit matching of the appearance of the data in the 2D image to the appearance of the data in the respective 3D images, wherein the slice identification and X,Y coordinates of a 3D image having a most similarly appearing pixel region to a corresponding X,Y region in the 2D region is selected. Potential importance of the respective objects and features in the synthesized 2D image is not taken into account for constructing the generic index map 108.

Figure 8:
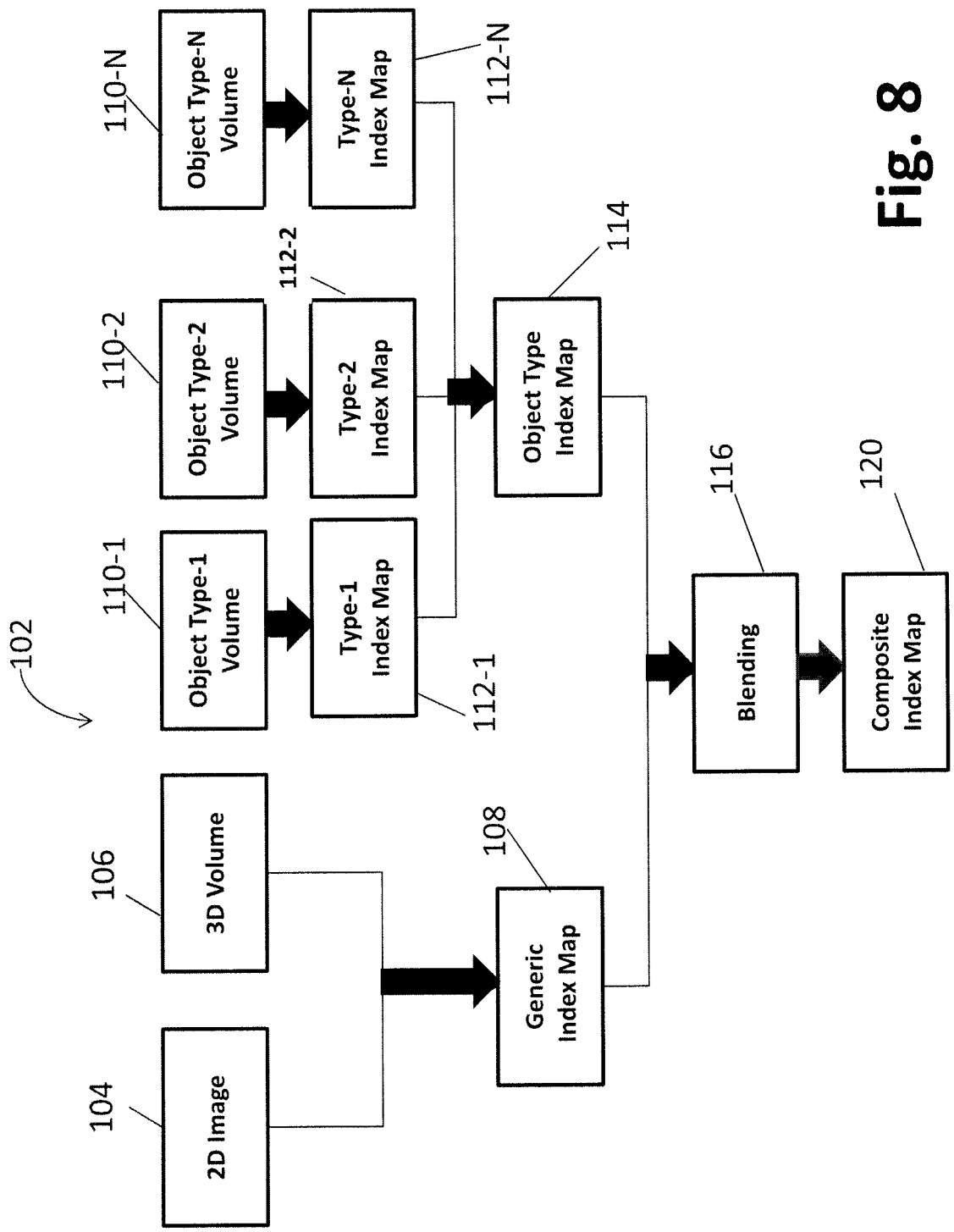
FIG. 8 is a flow diagram illustrating a process for constructing a composite index map of a synthesized 2D image to a corresponding reconstructed tomosynthesis image stack, according to still another embodiment of the presently disclosed technologies.

However, in parallel with the creation of the generic index map 108, an object type index map 114 is generated, in which individual object types, designated as 110-1 to 110-*n* in FIG. 8, in the synthesized 2D image are prioritized and assigned weighted values to influence the selection of the best corresponding 3D tomosynthesis image slice. In particular, an individual object type index map, designated as 112-1 to 112-*n* in FIG. 8, is generated for each object type identified in the synthesized 2D image, e.g., blob density, spiculated masses, micro-calcifications, etc. The individual object type index maps 112-1 to 112-*n* are then combined to construct the full object type index map 114, which is then blended, at step 116, with the generic index map 108 to provide a composite index map 120, wherein the object type image data is prioritized relative to the generic image data. The composite index map 120 is then used by the system for navigating the image slices of the 3D volume 106 in response to a selected or indicated location on the 2D image 104. In this manner, different object types having overlapping X,Y coordinates, i.e., due to their location at different z-axis positions in the volumetric breast image, can nevertheless be separately navigated for selective viewing, since separate mapping indexes are provided (See below example with respect to FIGS. 10 and 11).

As noted above, in various embodiments, an object or region may be automatically highlighted in the synthesized 2D image and/or displayed at least portion of the one or more images from the plurality. Additionally and/or alternatively, an object or region in the synthesized 2D image and/or displayed at least portion of the one or more images from the plurality may be highlighted in response to a further received user command or to certain user activity detected through the user interface. By way of non-limiting example, an object or region may is highlighted by a contour line representing a boundary of the highlighted object or region. Preferably, the object or region is highlighted in a manner indicating that the highlighted object or region is or contains a specified type of tissue structure.

By way of illustration, FIG. 9 depicts an exemplary work station display 122, including a left-hand side monitor 124 ("C-View") displaying a synthesized 2D image 132 of a patient's breast. The synthesized 2D image 132 includes a highlighted tissue structure 134, wherein the highlighting is in the form of a contour line that represents a boundary of the tissue structure. As noted above, this highlighting may have been done automatically by the system, e.g., at the time the 2D image 132 is initially displayed, or only in response to a specific user command or indication, e.g., by hovering a pointer over the object 134 in the 2D image 132. The work station display 122 also includes a right-hand side monitor 126 displaying the respective tomosynthesis image 136 (which is slice no. 18 of the tomosynthesis volume stack, as indicated in the lower right hand side of the monitor 126), which is the source image or which otherwise provides a most similar view of the highlighted tissue structure 134 as seen in the synthesized image 132. In particular, the user interface associated with the display 122 allows for a user to select or otherwise indicate a location on the synthesized 2D image 132, e.g., by displaying a pointer, a cross, a circle, or other similar geometrical object, and then input a certain command type (e.g., mouse click) that will be recognized by the system as a request from the user to have the corresponding source or otherwise most similar tomosynthesis slice(s) depicting the region or object underlying the pointer displayed in monitor 126.

FIG. 10 depicts the work station display 122, wherein a different synthesized 2D breast image 142 is displayed in the left-hand side C-View monitor 124. The synthesized 2D image 142 includes a highlighted tissue structure 144, wherein the highlighting is in the form of a geometric shape, in this case a circle, to indicate that the object 144 is a spiculated mass. Again, this highlighting may have been done automatically by the system, e.g., at the time the 2D image 142 is initially displayed, or only in response to a specific user command or indication, e.g., by hovering a pointer over the object 144 in the 2D image 142. The right-hand side monitor 126 is displaying the respective tomosynthesis image 146 (which is slice no. 33 of the tomosynthesis volume stack, as indicated in the lower right hand side of the monitor 126), which is the source image or which otherwise provides a most similar view of the highlighted tissue structure 144 as seen in the synthesized image 132.

It should be appreciated that there will be instances in which the mapping between an object or region in the merged 2D image to the respective object or region in the displayed (i.e., source or "best") image may not necessarily be 1-to-1, and will possibly be "1-to-many" in certain circumstances, for example, when multiple line structures on different tomosynthesis image slices combine together to form a line-crossing structures in the synthesized 2D image. By way of example, FIG. 11 depicts the user work station display 122, including the same synthesized 2D breast image 142 as displayed in FIG. 10, but now highlighting a region 154 containing micro-calcifications, with the right-hand side monitor displaying the tomosynthesis image slice 156 (which is slice no. 29 of the tomosynthesis volume stack, as indicated in the lower right hand side of the monitor 126), from which the highlighted region 154 was imported into the 2D image 142, or which otherwise provides a best view of the micro-calcifications. In particular, because the spiculated mass structure 144 and region of micro-calcifications 154 are in very close proximity in FIG. 14, a different one may be highlighted depending on a specific user command (e.g., to highlight a certain tissue type), or by slight adjustment of the position of the pointer of the user interface.

As explained above, this above described examples with respect to FIGS. 9-11 are readily accomplished by the index map constructed at the same time (or after—depending on the system implementation) the synthesized 2D image is generated. Alternatively, if no index map is available, for any given such user selected/specified point/location on the 2D image displayed in the left-hand-side monitor 124, the system may execute an algorithm to automatically compute the best corresponding image (i.e., X,Y and Z) within the tomosynthesis stack for display on the right-hand-side monitor 126. A "tomosynthesis slice indicator" may optionally be provided on the left-hand-side monitor 124, which indicates which tomosynthesis slice number (numbers) would be displayed on the right-hand-side monitor 126 based on a current location of a user curser on the 2D image. With this feature, the reviewer need not be distracted by constantly changing image displays on the right-hand-side monitor 126, while still providing the reviewer with an understanding of the z-axis location in the tomosynthesis volume stack of a particular object in the 2D image.

In accordance with a further aspect of the disclosed technologies, the available features of the user interface may be extended to function, not only based point/location of the merged image, but also based in a similar fashion on a structure/object/region. For example, particular objects or region(s) in the merged image may be automatically highlighted when displayed, based on the system recognition of possible interest in the respective objects, or of objects located in the respective region(s). In one embodiment, shown in FIG. 8, this highlighting is in the form of a contour line 108 that represents a boundary of a highlighted tissue structure. A contour line may be similarly used to highlight regions of interest in the displayed image, e.g., containing a number of calcification structures. In some embodiments, the system is configured to allow the user to "draw" a contour line on the merged image as a way of selecting or otherwise indicating an object or region of interest for causing the system to concurrently display one or more underlying source images of the selected or indicated object or region.

In preferred embodiments, the system employs known image processing techniques to identify different breast tissue structures in the various source images, and highlight them in the merged image, in particular, tissue structures comprising or related to abnormal objects, such as micro-calcification clusters, round-or-lobulated masses, spiculated masses, architectural distortions, etc.; as well as benign tissue structures comprising or related to normal breast tissues, such as linear tissues, cysts, lymph nodes, blood vessels, etc.

Furthermore, an object or region consisting of or containing a first type of tissue structure may be highlighted in a first manner in the displayed merged image, and an object or region consisting or containing a second type of tissue structure may be highlighted in a second manner different from the first manner in the displayed merged image.

In various embodiments, the user may input a command through the user interface selecting or otherwise identifying a certain type of tissue structure, and, in response to the received command, the system performs one or both of (i) automatically highlighting in the displayed merged image objects comprising the selected type of tissue structure and/or regions containing one or more objects comprising the selected type of tissue structure, and (ii) automatically concurrently displaying the respective source slice (or otherwise the slice with best depiction of) a tissue structure of the selected type in the breast image data, e.g., a most prominent one of the selected tissue structure type based on a comparison, if more than one is detected in the source image stack. Thus, when the user "click" on (or very close to) a micro-calcification spot/cluster in the merged 2D image, and the system automatically concurrently displays the source (or otherwise best) tomosynthesis image slice including the corresponding micro-calcification in 3D. By way of another example, a user can select (through the user interface) a region in the 2D merged image that has the appearance with radiating line patterns (often an indication of spiculated masses), and the system will concurrently display the source (or otherwise best) 3D tomosynthesis slice, or perhaps to a series of consecutive tomosynthesis slices, for viewing the radiating line patterns.

In various embodiments, the user may input a command through the user interface, activating dynamic display functionality, wherein the system automatically highlights those objects and tissue structures that (dynamically) correspond to the location of a user movable input device in the displayed merged image. In such embodiments, the system may further comprise automatically concurrently displaying a respective source image of a highlighted selected tissue structure that corresponds to a given location of a user movable input device in the displayed merged image, again, on a dynamic basis.

In one embodiment, the system can be activated to provide a "shadow" cursor is displayed on the right-hand-side monitor 126, in a location corresponding to the same (x,y) location as the user's actual curser on the left-hand-side monitor 124, so that moving the curser around in the 2D image moves the shadow curser in the tomosynthesis image at same X,Y coordinates. The reverse can also be implemented, i.e., with the active user curser operable in the right-hand monitor 126, and the show curser in the left-hand monitor 124. In one implementation, this dynamic display feature allows the system to follow the user's point of interest, e.g. mouse cursor location, in the 2d merged image, and dynamically display/highlight the most "meaningful" region(s) underneath in real time. For example, the user can move the mouse (without clicking any button) over a blood vessel, and the system will instantly highlight the vessel contour.

It should be appreciated that the presently disclosed technologies may be extended such that, rather than generate merely a synthesized 2D image and associated index/guidance map, the mapping concepts described herein may be extended to generate a fully mapped 3D volume, with each of the voxels in the mapped volume storing information related to the associated tomosynthesis slices(s) sourcing the particular voxel. For example, in one embodiment, the volume may be projected onto a fixed coordinate system, regardless of the actual volume of the breast. Projecting the volume to a fixed coordinate system in this manner facilitates processing of the image data, in particular, simplifying the correlation of voxels obtained during different acquisitions. For example, facilitating correlation of voxels in a 3D volume obtained from a CC acquisition of a breast with voxels in a volume obtained from an MLO acquisition of the same breast. In such an arrangement, one or more 3D maps may be provided, for example, to map from voxels in one slice of a 3D volume acquired via CC to one or more corresponding voxels in another volume, for example acquired via an MLO view. Such an arrangement facilitates comparison of slices obtained from different acquisitions that relate to a similar feature of interest within the breast volume, essentially permitting the medical professional to obtain a multi-planar review of a region of interest.

Tomosynthesis-Guided Biopsy Using a Synthesized Mammogram

Figure 12:
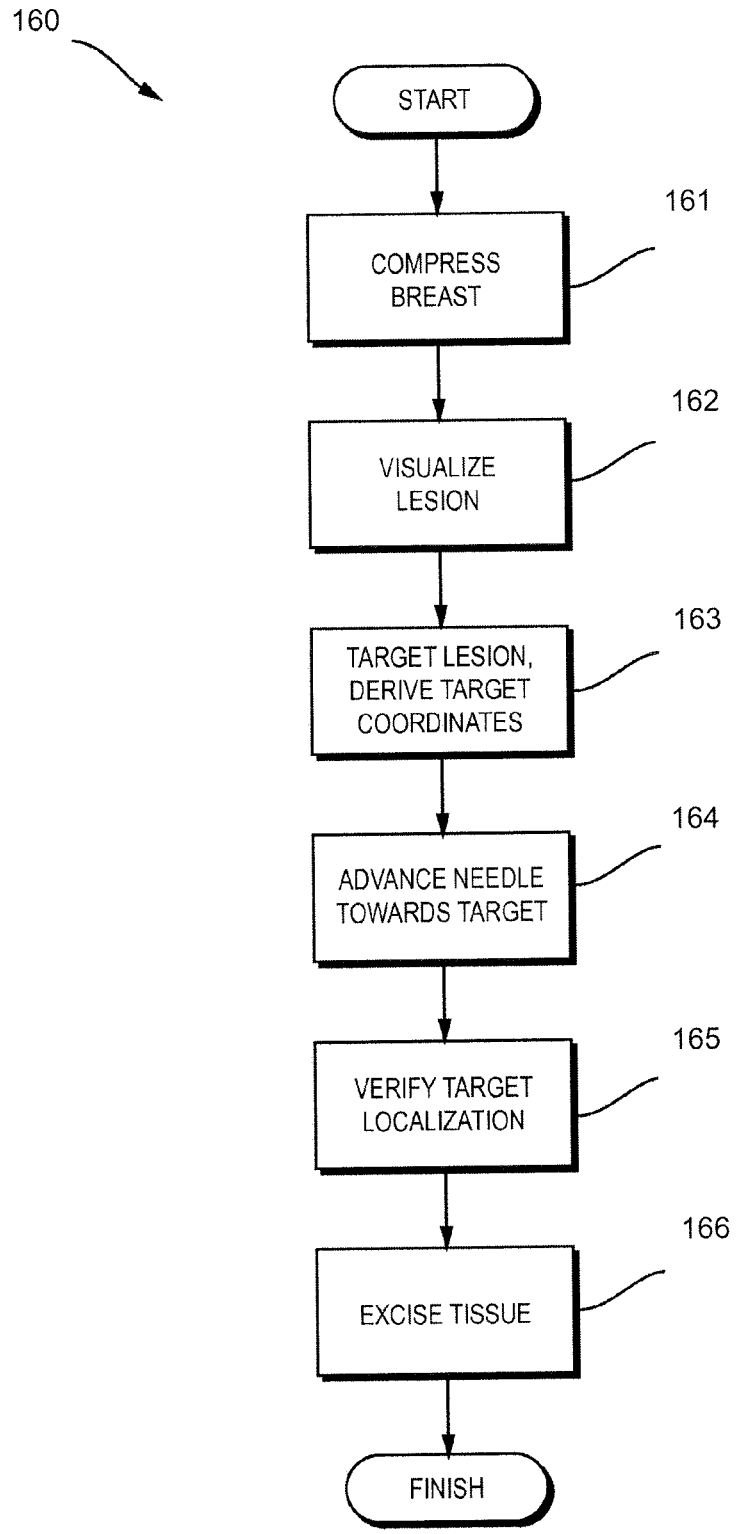
FIG. 12 is a flow diagram illustrating exemplary steps that may be performed during a biopsy using the targeting and presentation systems of the present technology.

In accordance with an embodiment of the present technology, as shown in FIG. 12, a multi-mode mammography/tomosynthesis system may be generally used as follows. A patient who has been identified as a candidate for biopsy is positioned at the multi-mode x-ray imaging system. At step 161 the biopsy compression paddle moves down towards the compression platform, compressing the patient's breast, and the process of visualizing the lesion is initiated at step 162. Depending upon the capabilities of the x-ray imaging system, visualization of the lesion can be performed utilizing a synthesized mammogram, in accordance with the embodiments described herein. Such an embodiment likely includes the lesion to be biopsied, unlike a first image presented in a stack of Tr images (alternatively referred to herein as tomo stack) commonly. Moreover, the synthesized mammogram better emulates the images that a doctor sees during traditional stereotactic biopsy. Using this mode may also save time scrolling through a tomo stack, since the synthesized mammogram optionally derives data from the tomo stack. In an additional embodiment, tomosynthesis mode can be used for a scout acquisition while still presenting the synthesized mammogram to a user in an effort to identify the relevant slice in the tomo stack in which the lesion is presented. Alternatively, visualization of the lesion may optionally use a scout image, a mammogram, acquired stereotactic images, acquired tomosynthesis projection images, tomosynthesis reconstructed images, or any combination thereof. In an additional or alternative embodiment, an x-ray imaging system having tomosynthesis capabilities may be adapted to include a "stereotactic mode," which, when selected, causes the x-ray imaging system to automatically retrieve the typical +/−15 degree stereotactic images and performs appropriate imaging processing on the stereotactic images to derive a stereotactic volume. One advantage of such an embodiment is that patient exposure may be reduced in tomosynthesis systems which use lower doses during projection image acquisition.

In an embodiment in which visualization of the lesion utilizes a synthesized mammogram, once the lesion has been visualized, at step 163 the lesion is targeted, either using the synthesized mammogram and/or the slice in the tomo stack to which the user is directed from the synthesized mammogram. Targeting the lesion may involve identifying the coordinates of the lesion using image data, and optionally converting the coordinates from the coordinate system of the images (e.g., a Cartesian coordinate system) to the coordinate system of the biopsy assembly using conversion techniques known to those of skill in the art. According to one aspect of the technology, different images, or combinations of images, may be used for visualizing the lesion than are used for targeting the lesion. In an embodiment, composite images, such as those described below with regard to FIG. 19 can be utilized for visualizing or targeting the lesion. In another example, assume that a scout image is initially used to ensure that the patient is in position, a pair of stereotactic images is used to visualize the lesion. If the lesion is found in the scout image, but not in both stereo images, the scout image may be used in combination with the stereotactic image in which the lesion is located to derive target location information. Therefore, as above, depending upon the capabilities of the x-ray imaging system, the lesion target coordinates may be derived using a scout image, a mammogram, a synthesized mammogram, acquired stereotactic images, acquired tomosynthesis projection images, tomosynthesis reconstructed images, or any combination thereof.

Figure 13:
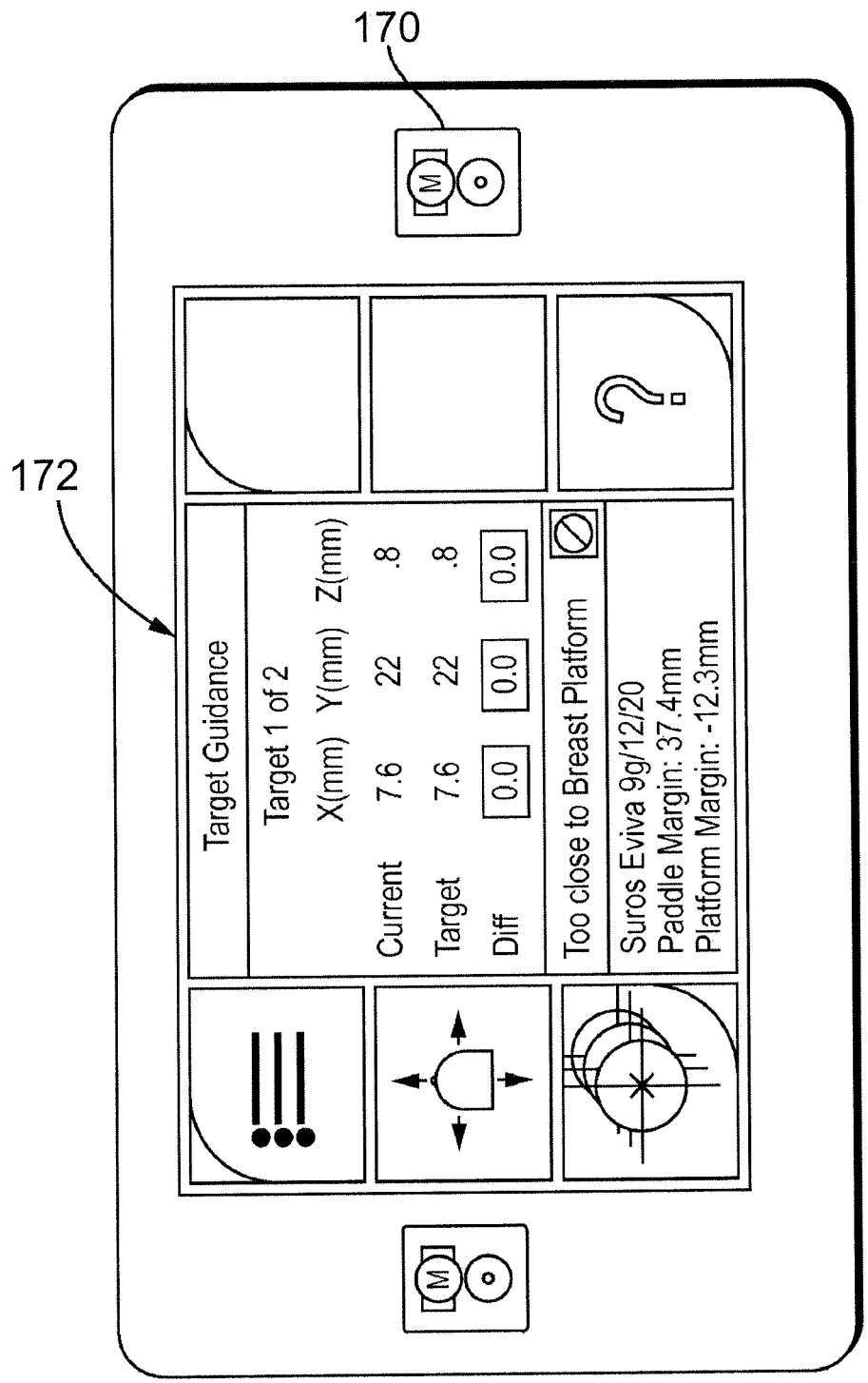
FIG. 13 illustrates an exemplary view of a user interface of the control unit of an image-guided biopsy system of the present technology.

At step 164, once the target coordinates are derived the user can begin the biopsy procedure by pressing control buttons required to move the biopsy needle. FIG. 13 illustrates an exemplary display and buttons of a control unit. The control unit includes a display 172 for displaying information related to the biopsy, such as information regarding needle size, distance to platform and paddle, needle coordinates, target coordinates, proximity to target and other related information. The control panel may also provide other helpful information to the user, such as warning indicators when the needle is too close to the breast platform, chest wall or skin line. As mentioned above, the warning indicators may be color coded or may provide other visual or audible indicators of undesirable conditions.

In one embodiment the control unit also includes buttons (including button 170) positioned and arranged to allow single handed activation of the biopsy assembly while precluding accidental activation. In one embodiment, a pair of control buttons is provided, one on the front face of the control panel, and another on the back face of the control panel. Biopsy assembly movement may only be activated via simultaneous depression of both buttons. Other mechanisms for affirming operator intent may be substituted herein without affecting the scope of the technology.

Returning now to FIG. 12, at step 165 once the needle has been advanced to the target coordinates, an image may be acquired to verify that, in fact, the needle is positioned at the lesion. If the biopsy needle is out of the view of the x-ray imaging system, such as that described in U.S. Patent Application Publication No. 2011/0087132, such image may be obtained without interference. At step 166, when it is verified that the needle is at the target, the tissue may be excised, and the biopsy is complete. Although not explicitly shown in the flow diagram, steps 165 and 166 may be repeated to verify excision of the entire lesion.

Figure 14:
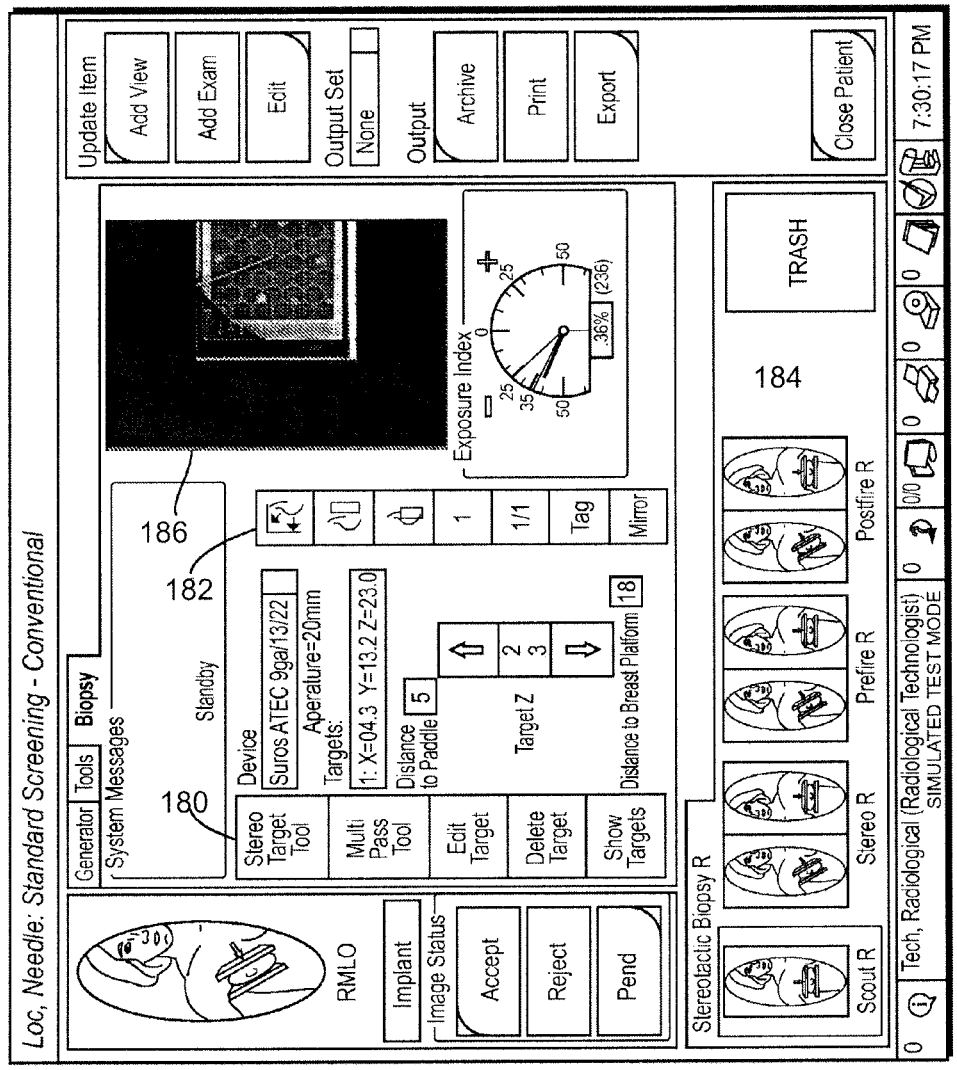
FIG. 14 illustrates an exemplary view of a user interface of an acquisition work station including functional modules and displays supporting and related to an image-guided biopsy in accordance with an embodiment of the present technology.

An example of user interface features that may be added to an acquisition workstation for use with a biopsy assembly is shown in FIG. 14. The user interface includes menus and/or control buttons or icons which enable the user to control the display and output of information gathered during the biopsy. Targeting tools 180 allow the user to review, modify and delete target information. Image source selectors 182 (including stereotactic, tomosynthesis, scout, mammography, etc.) allow the user to select which images to use for visualization or targeting. Image view selectors 184 allow the user to quickly pull up and view any of the images that may have been acquired during the biopsy. Any of the images may be pulled up in the image window 186. Other information related to the biopsy, such as the type of biopsy device, the relative distances between the target and the compression plate/platform, etc., may also be included on the acquisition workstation. It should be noted that although a particular arrangement of buttons and icons has been shown in the representative view of FIG. 14, the present technology is not limited to any particular representation of such information, and other forms of pull down menus, hyperlinks, icons, buttons, and windows are considered equivalents hereto.

Figure 15:
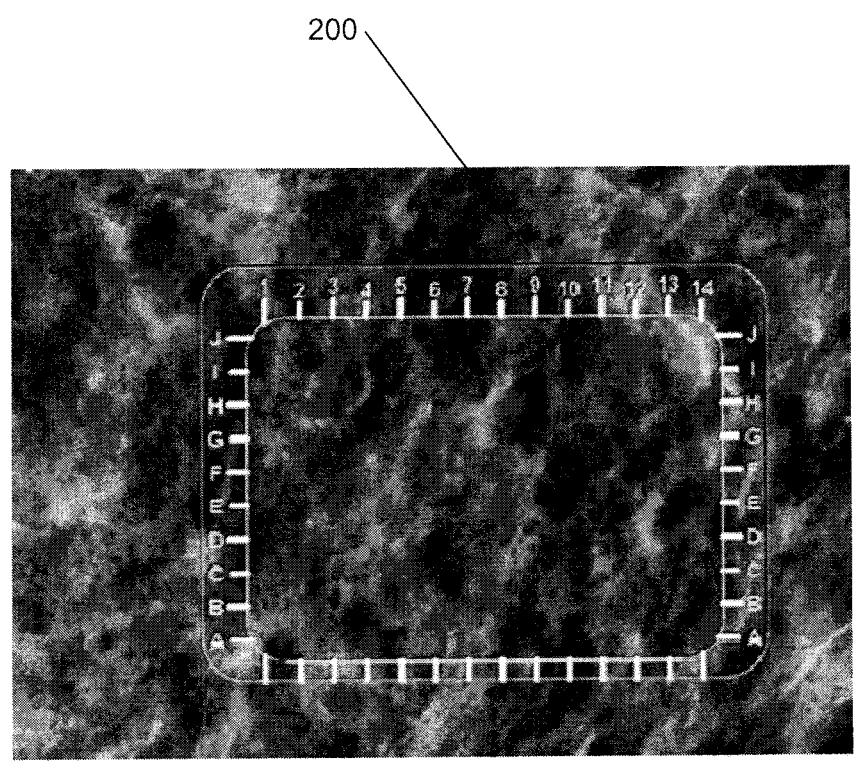
FIG. 15 illustrates an exemplary view of a portion of a user interface of an acquisition work station related to an image-guided biopsy according to an embodiment of the present technology.

In an additional embodiment in which the first image presented to a user is a synthesized mammogram, as shown in FIG. 15, the user interface may optionally include a biopsy window 200 overlaid on the synthesized mammogram. Such an interface aids the user in determining whether the patient is positioned correctly, which can help in saving time for the biopsy procedure. The biopsy window can optionally be toggled off and on by a user. The biopsy window can additionally or alternatively include an indication to the user if no calcium or mass is presented within the window. Such indication can be in the form of, but not limited to, an auditory or visual indication. In one nonlimiting example, determination of whether or not such an indication should be provided to the user is based at least in part on whether the biopsy window on the synthesized mammogram includes one of the features of the IMERGE map.

Moreover, in accordance with the embodiments described herein, presenting the synthesized mammogram to the user also facilitates navigating to a slice in the tomo stack in which the lesion or feature (e.g., abnormality, calcification, mass, etc.) is found. As an example, when a user selects a portion of the synthesized mammogram, the user can be directed to the slice in the tomo stack that best presents the lesion or feature in the synthesized mammogram. Alternatively, the user interface can be configured such that the user can be directed to a slice just above or below the slice in the tomo stack that presents the lesion or feature, which can be useful since a user may scroll through the tomo stack to be presented with varying views of the lesion or feature. In an additional embodiment, a visual target or indication can be placed automatically on the slice of interest in the tomo stack in response to a user selecting a lesion or feature on the synthesized mammogram presented to the user. Thus, a user can be directed to the lesion or feature on the relevant slice to correct the target for biopsy, e.g., by jogging in the X- or Y-directions or nudging in the Z-direction, if necessary. In additional or alternative embodiments, targets placed on the relevant slice can also be automatically placed or selected through use of CAD of calcification or mass enhancement in the synthesized mammogram. This could help with biopsy workflow as such selected targets or placements could be considered biopsy targets, which when used in combination with the biopsy window can ensure proper patient positioning. Such targets or placements can be independently verified by jumping to or scrolling through the slice(s) in the tomo stack.

Figure 16:
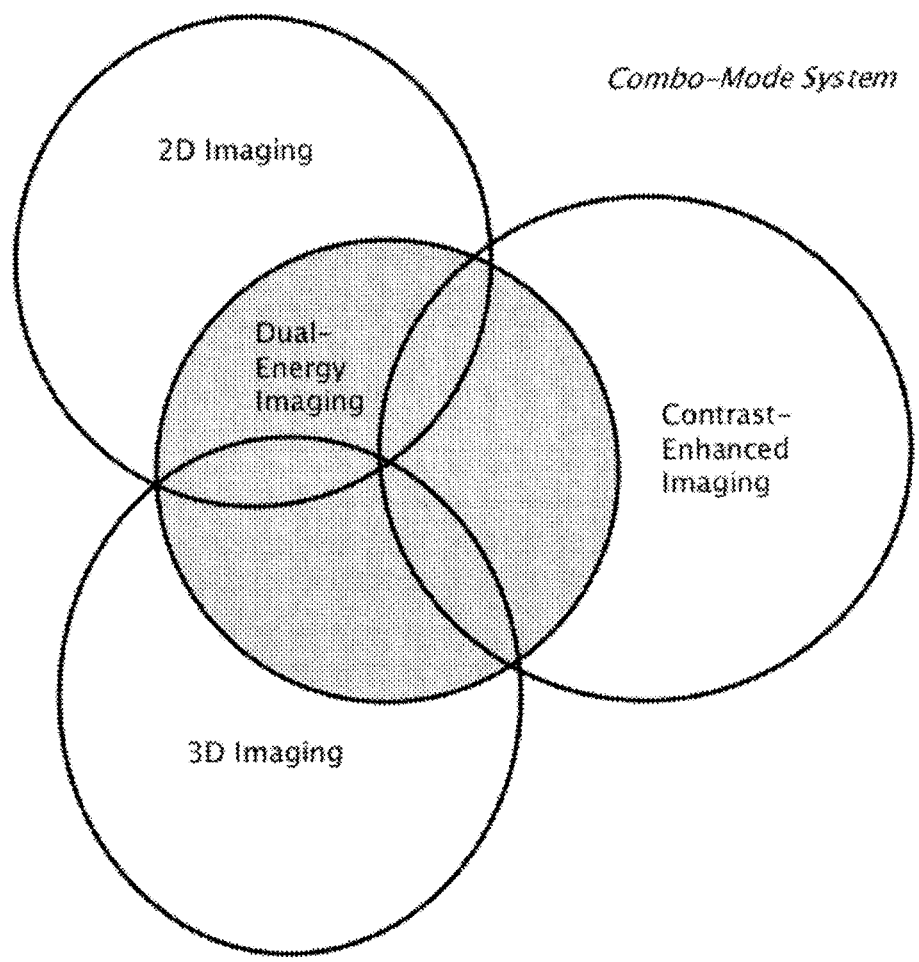
FIG. 16 illustrates possible combinations of imaging modes of a system in accordance with an embodiment of the present technology.
Figure 17:
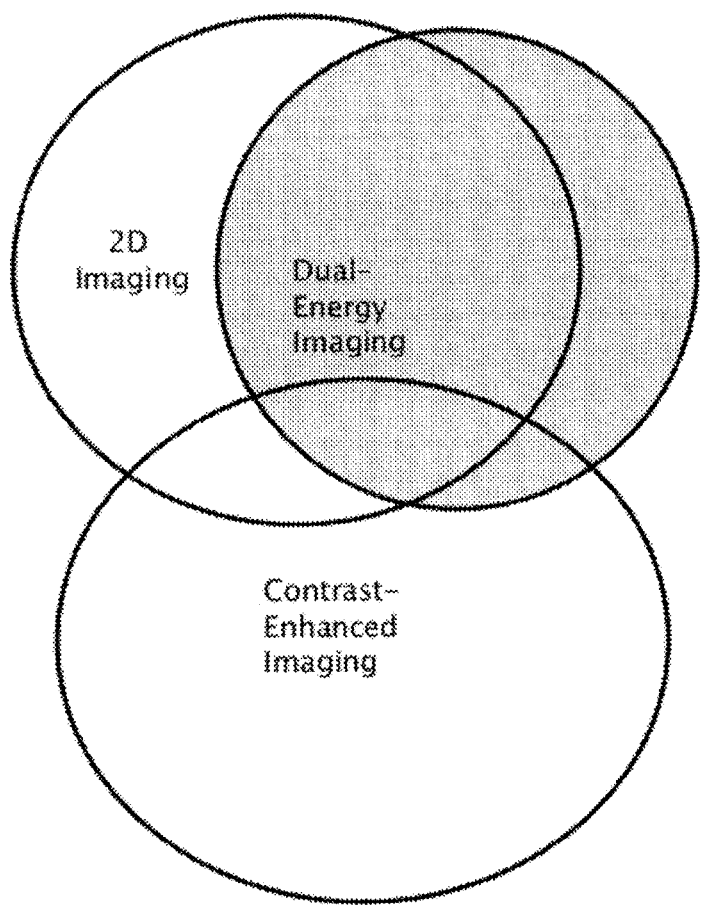
FIG. 17 illustrates possible combinations of imaging modes of a system according to an embodiment of the present technology, such as one that only takes 2D images.
Figure 18:
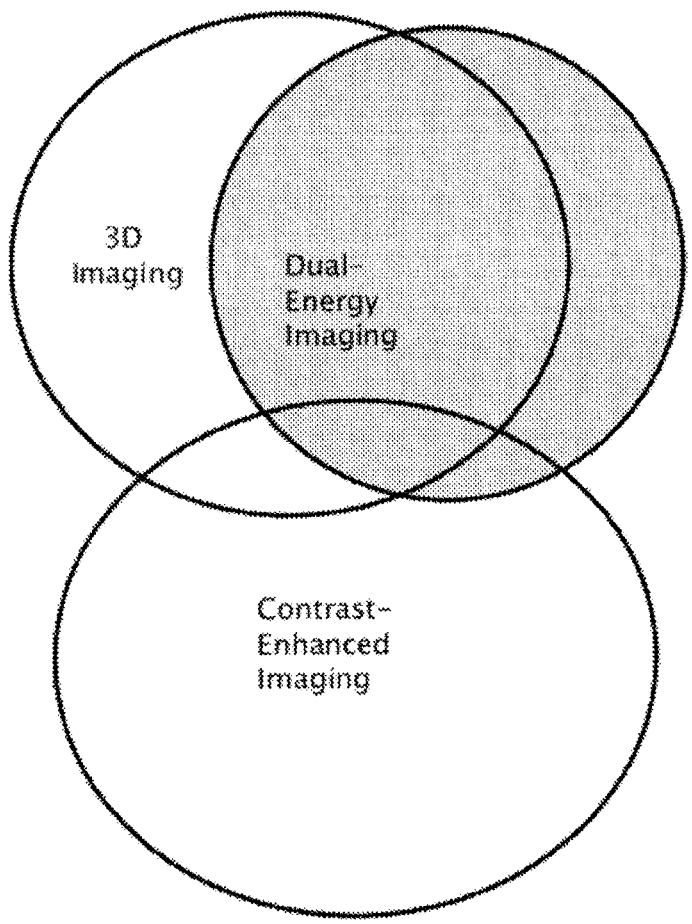
FIG. 18 illustrates possible combinations of imaging modes of a system in accordance with an embodiment of the present technology, such as one that only takes 3D images.

Image-Guided Biopsy Using Contrast Imaging, Dual Energy Imaging, and/or High Energy Imaging Image-guided biopsies in accordance with an embodiment of the technology may include use of one or more modes of contrast imaging, dual energy imaging, and/or high energy imaging, all in either 2D or 3D images. In dual energy imaging, multiple x-ray images are acquired—of one at low x-ray energy and one at high x-ray energy. Various aspects of x-ray energy may be varied such as dose, intensity, wavelength, and/or other aspects of x-ray energy known to those of skill in the art. The dual energy image may be a linear combination of the image pairs. In an embodiment, the dual energy image can be the difference between the high energy image and the low energy image. With respect to contrast imaging, a contrast agent can be visualized in the high energy image alone, which can optionally take the place and serve the same function as the dual energy image. Thus, reference to a contrast image can refer to either a dual energy image or a high energy image in which a contrast agent can be visualized. Contrast images can be either 2D or 3D or even synthesized 2D images, e.g., in which the contrast synthesized 2D image is derived from contrast 3D images and/or dual energy 3D image. Nonlimiting examples of such imaging systems are described at least at U.S. Patent Application Publication No. 2012/0238870. A breast imaging system according to examples described herein combines the capabilities of combined 2D and/or 3D breast x-ray imaging with benefits from contrast image acquisition processes. Biopsy capability (stereotactic or tomosynthesis guided) may also be integrated into the system, with lesion localization software (e.g., such as those described herein) utilizing any images selected from a group including 2D images (e.g., Mp), synthesized 2D images, 3D projection images, 3D reconstructed data. Additionally, images utilized may be selected from the group including any of the 2D (including synthesized 2D), 3D projection and 3D reconstructed data that were obtained utilizing a contrast, dual energy and/or background subtraction image acquisition process. With such arrangements, the following image protocols are supported: Contrast imaging (background subtraction) using a single high or low energy image acquisition technique, in 2D or 3D mode; Dual-energy contrast imaging in 2D or 3D mode; Dual-energy contrast imaging in 3D mode, wherein high and low energy exposures occur at different angles during a tomosynthesis scan; high and low energies can be reconstructed separately and combined to form the dual energy volume; Dual-energy imaging in a combo system that acquires dual-energy 2D and dual-energy 3D images; In combo imaging mode, where the 2D image data set is acquired using a single energy, and the 3D image data set is acquired using dual-energy imaging; In combo imaging mode, where the 2D image data set is acquired using dual-energy imaging, and the 3D image data set is acquired using a single energy image; Tomosynthesis imaging mode, wherein among a total of N views in a tomo scan, wherein the breast remains in compression throughout the scan, at least a subset of different projection images (or all of the different projection images) are allotted different dose, kVps, mAs and filters for greater flexibility of different applications; Tomosynthesis mode wherein low energy scans and high energy scans alternate in a series of acquired projection images; Tomosynthesis mode wherein low energy and high energy scans are performed for the projection images, in unequal ratios in user selectable patterns; biopsy (e.g., stereotactic or tomosynthesis) using contrast agent, and/or either dual energy, high energy, or background subtraction imaging; and/or Upright biopsy using tomosynthesis scan images obtained using a contrast agent, high energy, and/or dual-energy or background subtraction imaging. FIG. 16 illustrates a scope of imaging in different modes of operation of a combo system that operates in either or both of a 2D imaging mammography mode and a 3D imaging tomosynthesis mode. In each of these 2D and 3D modes, the system can image the breast with or without contrast agent in the breast. In either or both of the 2D and 3D modes, and with or without contrast agent in the breast, the system can carry out dual-energy imaging or background subtraction imaging. As seen in FIG. 16, these capabilities allow for many different combinations of modes such as 2D using single-energy (SE) and contrast enhancement (CE), 2D using SE, 3D using CE, 3D using DE, etc. FIG. 17 illustrates a scope of imaging when using a 2D only system, i.e., a system that does not include 3D tomosynthesis capabilities. In the FIG. 8 example, the system can be used in single-energy or dual-energy modes, in each case with or without contrast agent in the breast. FIG. 18 illustrates the operation of a 3D only system that can operate in 3D imaging mode using single-energy or dual-energy imaging, in either case with or without contrast agent in the breast.

A method of performing an x-ray contrast agent biopsy can comprise the following. A patient has an injection of the x-ray contrast agent. As an example, the patient is seated and given an IV injection of the contrast agent. A wait of typically 1-3 minutes occurs, which gives time for the contrast agent to accumulate in the breast tissue. The biopsy procedure using contrast agent can be similar to the non-contrast biopsy procedures that are well-known state of the art. The breast is compressed and one or more scout images are acquired to ensure that the lesion is appropriately centered in the biopsy paddle's opening. Unlike the non-contrast procedure, these scout images can be either dual-energy subtracted images or high energy images which visualize the contrast agent. The acquired images can be either 2D or 3D images. In an optional embodiment, the displayed image can be 2D (including synthesized 2D) and/or 3D images. Then, targeting commences. This can be done with a stereo pair of (typically acquired at)±15° dual energy or high energy 2D images, or one can target using the dual energy 3D scout image if that is available.

Some of the unique aspects of a contrast biopsy procedure and system relate to the short time that the contrast agent is present and visible in the breast. The visibility of the contrast agent changes with time and the visibility can be reduced during the length of time of the biopsy. Therefore, a user interface and/or targeting features are provided in which one can identify the lesion in the contrast agent image and correlate it to a reference object visible in the non-contrast agent low energy, normal 3D image (Tp or Tr), 2D image and/or synthesized mammogram. This would facilitate post-fire verification imaging to occur after the visibility of the lesion in the contrast agent has disappeared. This will also allow biopsying of multiple sites when the contrast agent might only be visible during the initial parts of the biopsy of the first lesion.

To aid in the correlation of a lesion identified in a contrast image to a structure seen in the normal low energy image, at least one or more of the following system features can be utilized. The display may be toggled to alternately show the low energy and the contrast image in the scout or stereo image pair. Coordinate crosshairs identified by the user may be saved in the contrast image and displayed on the low energy images. A crosshair may be located automatically on a standard tomo scout image and slice using crosshair locations or lesions identified by the user on the stereo contrast image. Alternatively or additionally, crosshairs may be automatically placed on stereo pairs (either low energy or contrast stereo pairs) from crosshairs or lesions identified on a tomo scout image that is either a standard low energy or a contrast scout image). Both the contrast image and the low energy image may be overlayed and/or simultaneously displayed on a single display, using different color maps for the two images.

Nonlimiting examples of biopsies in accordance with the systems described herein include any one or more of the following: a system capable of performing stereo biopsy and contrast stereo biopsy; a system capable of performing tomo biopsy and contrast tomo biopsy; a system capable of performing stereo and tomo and contrast stereo and contrast tomo biopsy; biopsy systems that have as part of their user interface methods of toggling a display between a contrast and a low energy image; biopsy systems that have as part of their user interface methods of simultaneously superimposing and displaying a low energy and a contrast image; a system that allows marking crosshair locations in contrast images and displaying them on low energy images, to allow a biopsy procedure and verification to occur when the contrast agent is no longer visible on the image due to the time elapsed during the procedure; a procedure of performing a biopsy using x-ray contrast guided imaging; a prone biopsy system that utilizes two or more x-ray filters, e.g., one filter is used for the low energy image, and another filter for the high-energy image, the high energy filter preferably contains copper; and/or an x-ray contrast biopsy system and procedure where some of the images are taken at a low kV and others are taken at a high kV above the k-edge of iodine.

Figure 19:
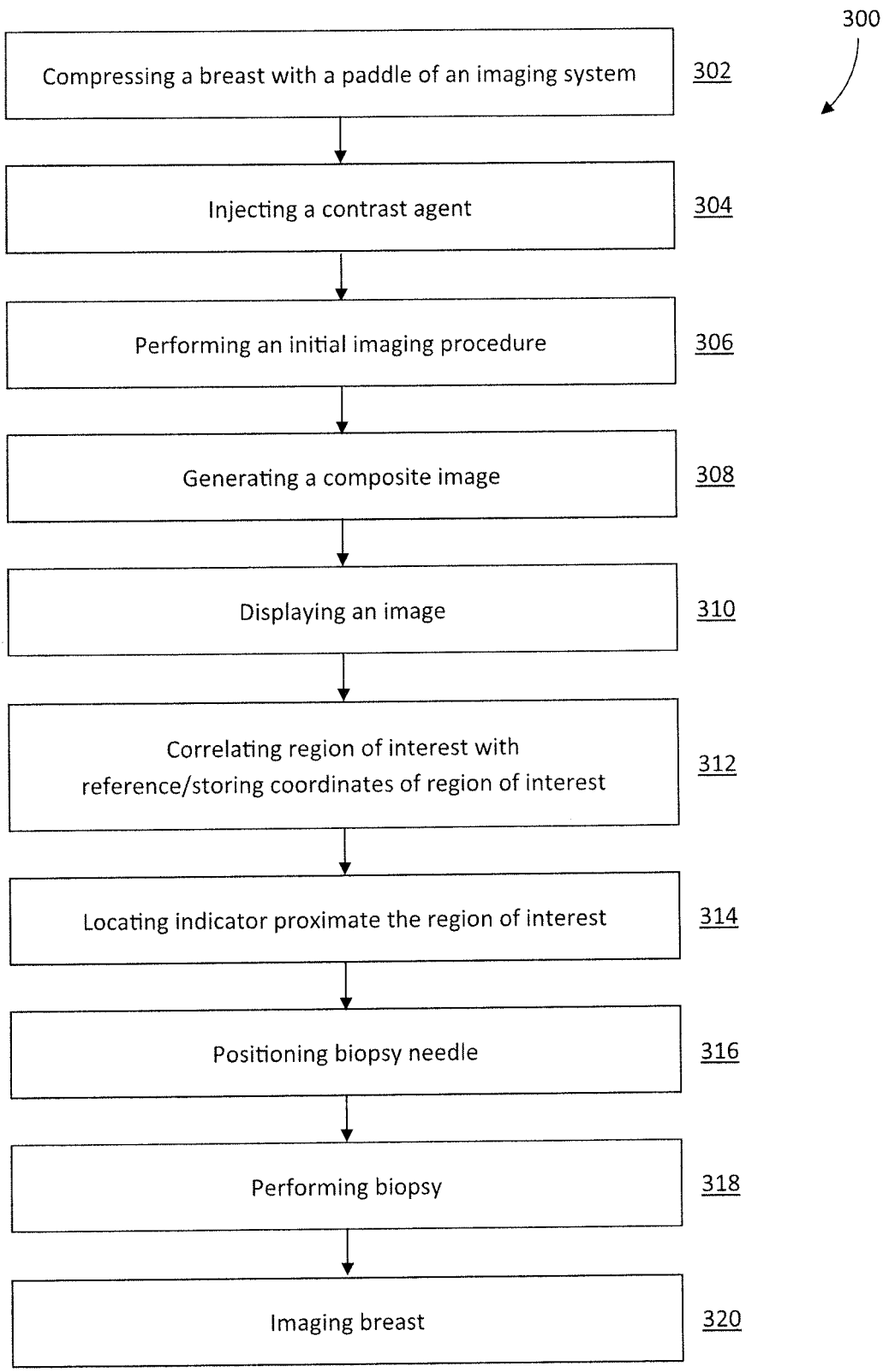
FIG. 19 depicts a method of performing a procedure on a breast of a patient.

With the above descriptions in mind, FIG. 19 depicts one method 300 of performing a procedure, such as a biopsy, on a breast of a patient. Other methods consistent with the disclosures herein are contemplated. In operation 302, the breast is compressed with a paddle of an imaging system, typically between the paddle and an associated platform. If contrast imaging is to be performed, a contrast agent may be injected into the patient before or after compression of the breast, operation 304. The amount of time between injection and imaging can be as required or desired for a particular contrast agent, patient specifics, technician experience, etc.

An initial imaging procedure is then performed, operation 306. The imaging operation can include imaging the breast a plurality of times at predetermined dosages, which may be the same, substantially the same, or different. Indeed, if contrast imaging is performed, the first dosage may be higher than a subsequent dosage, such that the contrast agent is readily visible in an image resulting from the first imaging procedure. Dual energy imaging may also utilize two different dosages. Each imaging procedure may generate a discrete image that may be stored or processed as described below.

A composite image (e.g., a combination of the plurality of images, one such combination being a substitution of a first image from a second image) can be generated, operation 308. Any of the various images resulting from each imaging procedure, or the composite image, can be displayed to a user, operation 310, for further analysis or study. Differences in the plurality of images may be indicative of a region of interest, which may be identified on the displayed image. A spatial position of the region of interest within the breast may be correlated with a reference object in the image, or the coordinates of the region of interest may be stored, operation 312. By identifying the region of interest and storing the coordinates thereof (or a location relative to a reference object visible in the displayed image), the region of interest may be targeted for further procedures, such as a biopsy. Additionally, an indicator may be located so as to mark a region of interest within the breast, operation 314. This indicator may be located by action of a user of the system (e.g., an operator touching a screen), or the system may automatically mark a region of interest to draw attention thereto. Once the region of interest is targeted, a biopsy needle may be positioned, operation 316. Positioning may be performed manually or automatically, based on the various types of information stored on the system. Once positioned as required or desired, a biopsy may be performed, operation 318. Thereafter, to confirm the region of interest was properly targeted, the breast may be imaged again, operation 320.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

All parts, ratios, and percentages herein, in the Detailed Description and Claims are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All documents cited herein are, in the relevant part, incorporated herein by reference; the citation of any document is not to be construed as an admission that it is prior art with respect to the present technology. To the extent that any meaning or definition of a term or in this written document conflicts with any meaning or definition in a document incorporated by reference, the meaning or definition assigned to the term in this written document shall govern.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed technologies. Thus the above specific embodiments are illustrative, and many variations can be introduced on these embodiments without departing from the scope of the appended claims.

What is claimed is:

1. A method of performing a procedure on a breast of a patient, the method comprising:
   compressing the breast of the patient with a paddle of an imaging system, wherein the imaging system includes an x-ray source and a receptor;
   performing a 2D imaging procedure on the breast of the patient during a single breast compression, wherein the 2D imaging procedure comprises imaging the breast and a contrast agent disposed therein with the x-ray source at a first energy to obtain a first image at the receptor and a second energy to obtain a second image at the receptor, and wherein the first energy is different than the second energy;
   generating a composite 2D image from the first image and the second image;
   displaying the composite 2D image and a region of interest in the composite 2D image, wherein the region of interest comprises an abnormality;
   identifying the region of interest in the composite 2D image;

performing a 3D imaging procedure on the breast of the patient during the single breast compression, wherein the 3D imaging procedure comprises imaging the breast with the x-ray source to obtain a plurality of projection images at the receptor and reconstructing the plurality of projection images in a 3D image set;

correlating the region of interest in the composite 2D image with a reference object in the 3D image set;

receiving, in the 3D image set, a selection of the region of interest;

inserting a marker proximate a target location in the breast; and performing a biopsy on the target location in the breast based on the selection in the 3D image set, wherein the target location corresponds to the reference object in the 3D image set.

2. The method of claim 1, further comprising using information from the composite 2D image to define the target location.

3. The method of claim 1, wherein
identifying the region of interest visible in the composite 2D image comprises receiving a selection of the region of interest.

4. The method of claim 1, further comprising locating an indicator proximate the region of interest on the composite 2D image.

5. The method of claim 1, further comprising storing coordinates of the region of interest.

6. The method of claim 5, further comprising positioning a biopsy needle based at least in part on the stored coordinates.

7. The method of claim 1, further comprising injecting the patient with the contrast agent prior to imaging at the first energy, such that the contrast agent is visible in the first image.

8. The method of claim 1, wherein the composite 2D image is a synthesized 2D image.

9. The method of claim 1, wherein the composite 2D image comprises a subtracted image.

10. The method of claim 1, further comprising simultaneously displaying the first image and the second image.

11. The method of claim 1, further comprising displaying an overlay of the first image and the second image.

12. The method of claim 1, further comprising, after performing the biopsy on the target location, post-fire imaging the breast with the x-ray source at a third energy to obtain a third image.

13. The method of claim 12, wherein the first energy and the second energy are different than the third energy, and wherein the third energy is emitted during the single breast compression.

14. The method of claim 12, further comprising displaying the third image.

15. The method of claim 1, further comprising identifying at least one difference between the first image and the second image, wherein the difference corresponds to the region of interest.

16. A method of performing a procedure on a breast of a patient, the method comprising:

compressing the breast of the patient with a paddle of an imaging system, wherein the imaging system includes an x-ray source and a receptor;

performing a 2D imaging procedure on the breast of the patient during a single breast compression, wherein the 2D imaging procedure comprises imaging the breast and a contrast agent disposed therein with the x-ray source at a first energy to obtain a first image at the receptor and a second energy to obtain a second image at the receptor, and wherein the first energy is different than the second energy;

generating a composite 2D image from the first image and the second image;

displaying the composite 2D image and a region of interest in the composite 2D image, wherein the region of interest comprises an abnormality;

performing a 3D imaging procedure on the breast of the patient during the single breast compression, wherein the 3D imaging procedure comprises imaging the breast with the x-ray source to obtain a plurality of projection images at the receptor and reconstructing the plurality of projection images in a 3D image set;

receiving, in at least one of the composite 2D image and the 3D image set, a selection of the region of interest;

correlating the region of interest in the composite 2D image with a reference object in the 3D image set;

storing coordinates associated with the reference object; and inserting a marker proximate a target location in the breast that corresponds to the reference object.

17. The method of claim 16, further comprising displaying, concurrently with the composite 2D image, at least one of the plurality of projection images in the 3D image set.

18. The method of claim 17, further comprising:
receiving the user selection of the region of interest in the composite 2D image; and
identifying the selected region of interest in the 3D image set based on the user selection in the composite 2D image.

19. A method of performing a procedure on a compressed breast of a patient, the method comprising:

initiating a 2D imaging procedure on the compressed breast of the patient during a single breast compression, wherein the 2D imaging procedure comprises imaging the compressed breast and a contrast agent disposed therein with the x-ray source at a first energy to obtain a first image at a receptor and a second energy to obtain a second image at the receptor, and wherein the first energy is different than the second energy;

generating a composite 2D image from the first image and the second image;

displaying the composite 2D image and a region of interest in the composite 2D image, wherein the region of interest comprises an abnormality;

initiating a 3D imaging procedure on the compressed breast of the patient during the single breast compression, wherein the 3D imaging procedure comprises imaging the compressed breast with the x-ray source to obtain a plurality of projection images at the receptor and reconstructing the plurality of projection images in a 3D image set;

correlating the region of interest in the composite 2D image with a reference object in the 3D image set;

receiving, in at least one of the composite 2D image and the 3D image set, a user selection of at least one of the region of interest and the reference object;

storing coordinates associated with the reference object; and inserting a marker proximate a target location in the breast that corresponds to the reference object.

20. The method of claim 1, wherein the first energy is greater than the second energy.

21. The method of claim 1, wherein the second energy is greater than the first energy.

* * * * *